US011435338B2

(12) United States Patent
Zhao et al.

(10) Patent No.: US 11,435,338 B2
(45) Date of Patent: Sep. 6, 2022

(54) FRACTIONAL ABUNDANCE OF POLYNUCLEOTIDE SEQUENCES IN A SAMPLE

(71) Applicant: Ontera Inc., Santa Cruz, CA (US)

(72) Inventors: Yanan Zhao, Felton, CA (US); William McKenna, Santa Cruz, CA (US); William B. Dunbar, Santa Cruz, CA (US)

(73) Assignee: Ontera Inc., Santa Cruz, CA (US)

(*) Notice: Subject to any disclaimer, the term of this patent is extended or adjusted under 35 U.S.C. 154(b) by 0 days.

(21) Appl. No.: 16/098,803

(22) PCT Filed: Oct. 24, 2017

(86) PCT No.: PCT/US2017/058159
§ 371 (c)(1),
(2) Date: Nov. 2, 2018

(87) PCT Pub. No.: WO2018/081178
PCT Pub. Date: May 3, 2018

(65) Prior Publication Data
US 2020/0225210 A1 Jul. 16, 2020

Related U.S. Application Data

(60) Provisional application No. 62/412,221, filed on Oct. 24, 2016.

(51) Int. Cl.
*G01N 33/487* (2006.01)
*G01N 27/447* (2006.01)
*C12Q 1/6876* (2018.01)

(52) U.S. Cl.
CPC ..... *G01N 33/48721* (2013.01); *C12Q 1/6876* (2013.01); *G01N 27/44791* (2013.01)

(58) Field of Classification Search
CPC ......... G01N 27/44791; G01N 27/4473; G01N 33/48721; G01N 33/48728; G01N 33/68; C12Q 1/6813; C12Q 1/6876; C12Q 1/6825; C12Q 1/686; C12Q 1/6806; C12Q 2545/114
See application file for complete search history.

(56) References Cited

U.S. PATENT DOCUMENTS

| | | | |
|---|---|---|---|
| 4,446,235 A | 5/1984 | Seeburg | |
| 6,211,956 B1 | 4/2001 | Nicoli | |
| 6,287,772 B1 | 9/2001 | Stefano et al. | |
| 8,764,968 B2 | 7/2014 | Afzali-Ardakani et al. | |
| 8,764,986 B2 | 7/2014 | Afzali-Ardakani et al. | |
| 2003/0104428 A1 | 6/2003 | Branton et al. | |
| 2003/0108913 A1 | 6/2003 | Schouten et al. | |
| 2005/0033520 A1 | 2/2005 | Dai et al. | |
| 2006/0073489 A1 | 4/2006 | Li et al. | |
| 2007/0178470 A1 | 8/2007 | Bissonnette et al. | |
| 2007/0190542 A1 | 8/2007 | Ling et al. | |
| 2007/0190543 A1 | 8/2007 | Livak | |
| 2008/0218184 A1 | 9/2008 | White et al. | |
| 2009/0298080 A1 | 12/2009 | Hanna et al. | |
| 2010/0035260 A1 | 2/2010 | Olasagasti et al. | |
| 2010/0099198 A1 | 4/2010 | Zhao et al. | |
| 2010/0145037 A1 | 6/2010 | Makarov et al. | |
| 2010/0261285 A1 | 10/2010 | Goldstein et al. | |
| 2010/0291548 A1 | 11/2010 | Sharaf et al. | |
| 2010/0331194 A1 | 12/2010 | Turner et al. | |
| 2011/0124518 A1 | 5/2011 | Cantor | |
| 2012/0214162 A1 | 8/2012 | Oliver | |
| 2012/0289426 A1 | 11/2012 | Roos et al. | |
| 2013/0040827 A1 | 2/2013 | Macevicz | |
| 2013/0092541 A1 | 4/2013 | Drndic et al. | |
| 2013/0109577 A1 | 5/2013 | Korlach et al. | |
| 2013/0231473 A1 | 9/2013 | Brown et al. | |
| 2013/0260472 A1 | 10/2013 | Holt | |
| 2013/0327644 A1 | 12/2013 | Turner et al. | |
| 2014/0158540 A1 | 6/2014 | Ohura | |
| 2014/0287946 A1 | 9/2014 | Marble | |
| 2014/0356867 A1 | 12/2014 | Peter et al. | |
| 2015/0037249 A1 | 2/2015 | Fu | |
| 2015/0133319 A1 | 5/2015 | Fu et al. | |
| 2015/0159213 A1 | 6/2015 | Turner et al. | |
| 2016/0266089 A1 | 9/2016 | Morin et al. | |
| 2018/0155768 A1 | 6/2018 | Cohen et al. | |

FOREIGN PATENT DOCUMENTS

| | | |
|---|---|---|
| CN | 102224259 A | 10/2011 |
| CN | 103421896 A | 12/2013 |
| CN | 103451265 A | 12/2013 |
| CN | 104145026 A | 11/2014 |

(Continued)

OTHER PUBLICATIONS

Patent Cooperation Treaty, International Search Report and Written Opinion of the International Searching Authority, International Patent Application No. PCT/US2017/058159, 14 Pages, dated Dec. 26, 2017.
Chinese National Intellectual Property Administration, Office Action, Chinese Application No. 201580064356.4, dated Apr. 2, 2020, 14 pages (with concise explanation of relevance).
Intellectual Property India, Examination Report, IN Patent Application No. 201847041305, dated Oct. 12, 2020, six pages.
United States Office Action, U.S. Appl. No. 15/513,472, filed Oct. 23, 2020, 27 pages.
Japan Patent Office, Office Action, Japanese Application No. 2018-562343, dated Apr. 10, 2019, 8 pages.
Korean Intellectual Property Office, Office Action, Korean Application No. 10-2018-7034922, dated Mar. 19, 2019, 10 pages (with concise explanation of relevance).
Extended European Search Report, European Application No. 17776864.5, October 7, 2019, 9 pages.

(Continued)

*Primary Examiner* — Gurpreet Kaur
(74) *Attorney, Agent, or Firm* — Fenwick & West LLP

(57) ABSTRACT

Disclosed herein are methods and compositions for determining an improved estimate of the true fractional abundance of target analytes (e.g., specific polynucleotide sequences) in a sample using a nanopore sensor, e.g., by correcting errors inherent to identifying and correlating electrical signals to amounts of a target analyte or reference analyte in a sample.

41 Claims, 19 Drawing Sheets

(56) References Cited

FOREIGN PATENT DOCUMENTS

| CN | 104937111 A | 9/2015 |
|---|---|---|
| CN | 106471369 A | 3/2017 |
| JP | 2014-020837 A | 2/2014 |
| KR | 10-2006-0071772 | 6/2006 |
| WO | WO 2009/092035 A2 | 7/2009 |
| WO | WO 2012/121756 A1 | 9/2012 |
| WO | WO 2013/012881 A2 | 1/2013 |
| WO | WO 2014/182634 A1 | 11/2014 |
| WO | WO 2015/138405 A2 | 9/2015 |
| WO | WO 2015/171169 A1 | 11/2015 |
| WO | WO 2015/176034 A1 | 11/2015 |
| WO | WO 2016/049657 A1 | 3/2016 |
| WO | WO 2016/126746 A1 | 8/2016 |
| WO | WO 2016/126748 A1 | 8/2016 |
| WO | WO 2016/187159 A2 | 11/2016 |
| WO | WO 2017/173392 A1 | 10/2017 |
| WO | WO 2016/136952 A1 | 11/2017 |
| WO | WO 2018/093976 A1 | 5/2018 |

OTHER PUBLICATIONS

Boser, B.E. et al., "A training algorithm for optimal margin classifiers," Proceedings of the Fifth Annual Workshop on Computation Learning Theory, 1992, 9 pages.
Cortes, C. et al., "Support-Vector Networks," Machine Learning, 1995, vol. 20, pp. 273-297.
Demers, L.M. et al., "A Fluorescence-Based Method for Determining the Surface Coverage and Hybridization Efficiency of Thiol-Capped Oligonucleotides Bound to Gold Thin Films and Nanoparticles," Analytical Chemistry, Nov. 15, 2000, vol. 72, No. 222, p. 5540.
Extended European Search Report, European Application No. 17865592.4, dated Jan. 18, 2019, 9 pages.
Fologea, D. et al., "Detecting Single Stranded DNA with a Solid State Nanopore," Nano Letters, Oct. 2005, vol. 5, No. 10, pp. 1905-1909.
Gierhart, B.C. et al., "Nanopore with Transverse Nanoelectrodes for Electrical Characterization and Sequencing of DNA," Sensors and Actuators, Jun. 16, 2008, vol. 132, No. 2, pp. 1-21.
Gong, H. et al., "Simple Method to Prepare Oligonucleotide-Conjugated Antibodies and Its Application in Multiplex Protein Detection in Single Cells," Bioconjugate Chemistry, Jan. 4, 2016, vol. 27, No. 1, pp. 215-217.
IP Australia, First Office Action, Australian Application No. 2017348009, dated Dec. 7, 2018, 7 pages.
Lau, L.T. et al., "Detection and Characterization of Recombinant DNA in the Roundup Ready Soybean Insert," Food Control, Sep. 30, 2004, vol. 15, No. 6, p. 474.
Liu, L et al., "Selective Detection of 8-Oxo-2'-deoxyguanosine in Single-Stranded DNA via Nanopore Sensing Approach," Analytical Chemistry, Dec. 29, 2015, vol. 88, No. 2, pp. 1-15.
Morin, T. J. et al., "Nanopore-based target sequence detection." PloS one, May 5, 2016, vol. 11, No. 5, , pp. e0154426.
Paris, C. et al., "Exploiting Protected Maleimides to Modify Oligonucleotides, Peptides and Peptide Nucleic Acids," Molecules, Apr. 10, 2015, vol. 20, No. 4, pp. 6389-6408.
PCT International Preliminary Report on Patentability, PCT Application No. PCT/US2017/025585, dated Dec. 13, 2018, 37 pages.
PCT International Search Report and Written Opinion, PCT Application No. PCT/US2017/25585, dated Jul. 20, 2017, 22 pages.
Quick, J. et al., "A Reference Bacterial Genome Dataset Generated on the MinION Portable Single-Molecule Nanopore Sequencer," Gigascience, Oct. 20, 2014, vol. 3, No. 2, p. 2.
Storm, A.J. et al., "Translocation of double-strand DNA through a silicon oxide nanopore", Physical Review E, 2005, vol. 71, p. 051903-1 to 051903-10.
Yanagi, I. et al., "Fabricating Nanopores with Diameters of Sub-1 Nm to 3 Nm using Multilevel Pulse-Voltage Injection," Scientific Reports, 2014, vol. 4, p. 5000.
Zhou, S. et al., "Label-free nanopore single-molecule measurement of trypsin activity." ACS Sensors, Mar. 24, 2016, vol. 1, pp. 607-613.
China National Intellectual Property Administration, Office Action, CN Patent Application No. 201780031347.7, dated Jan. 21, 2021, 13 pages.
European Patent Office, Extended European Search Report and Opinion, EP Patent Application No. 20205185.0, dated Mar. 3, 2021, ten pages.
Sciencedirect, "Avidin", Date Unknown, ten pages, [Online] [Retrieved on Jan. 8, 2021] Retrieved from the Internet <URL: https://www.sciencedirect.com/topics/neuroscience/avidin>.
United States Office Action, U.S. Appl. No. 16/079,762, filed Jan. 15, 2021, 36 pages.
Osaki, T. et al., "Multichannel Simultaneous Measurements of Single-Molecule Translocation in α-Hemolysin Nanopore Array," Analytical Chemistry, vol. 81, Iss. 24, Nov. 12, 2009, pp. 9866-9870.
United States Office Action, U.S. Appl. No. 16/391,176, filed Dec. 13, 2021, 11 pages.

$$\rho(q) = \frac{Q_{mix}(q) - Q_{ref}(q)}{Q_{targ}(q) - Q_{mix}(q)}$$

FRACTIONAL ABUNDANCE OF POLYNUCLEOTIDE SEQUENCES IN A SAMPLE

CROSS REFERENCE TO RELATED APPLICATIONS

This application is a 35 U.S.C. 371 national stage filing of International Application No. PCT/US2017/058159, filed on Oct. 24, 2017, which claims the benefit of U.S. Provisional Application No. 62/412,221, filed Oct. 24, 2016, and International Application No. PCT/US2017/025585, filed Mar. 31, 2017, the contents of which are each incorporated by reference in their entirety.

FIELD OF THE INVENTION

A method to determine the fractional abundance of specific polynucleotide sequences from a sample using solid state nanopores and mathematical methods for precise and accurate quantitation.

BACKGROUND OF THE INVENTION

Characterization of a liquid sample by determining a relative abundance of components present in the sample can provide valuable information for many scientific fields and applications. For example, a relative abundance of a point mutation in circulating cell free DNA can be used to diagnose or monitor progression of cancer in a patient. As another example, determining the fractional amount of a transgenic sequence of a genetically modified organism (GMO) to the non-GMO reference sequence within genomic DNA, obtained from a collection of seeds for example, is important for regulatory and economic reasons.

Some methods exist for sensitive detection of a fractional amount of a target analyte in a sample, however, these methods are usually expensive and time-consuming, or have other limitations. For example, quantitative real-time PCR (qPCR) assays remain the standard method used to determine the relative quantity of target nucleic acid sequences to an invariant reference sequence within a test sample. The quantitative performance of qPCR is, however, limited by variability in amplification efficiencies per sample, and per amplicon. Factors that affect amplification efficiency include inhibitors and carryover contaminants from the sample substrate and the extraction reagents themselves. These factors vary by sample and prep, but also in the degree to which they affect the amplification efficiency of one sequence versus another. Slight, variable differences in the amplification efficiency of target versus reference amplicons limit qPCR to resolving quantity differences >1.5x-fold. Furthermore, amplification reactions require specialized reagent sets and must be properly stored, and can be time consuming and sensitive to reaction conditions.

The use of nanopore devices have emerged as a sensitive tool for single molecule identification, wherein individual molecules are identified upon translocation through the nanopore under an applied voltage. Nanopore devices are amenable to point of use applications, and be sufficiently inexpensive and efficient for routine daily use cases, in human health, agriculture, or anywhere else. However, the use of data from a nanopore can be subject to errors that can impact a determination of quantitative estimates of analytes in a sample, such that the reliable use of this data is not feasible.

What is needed, therefore, are improved methods of determining fractional abundance of a target analyte compared to a reference analyte in a sample that are versatile, inexpensive and easy to use.

SUMMARY OF THE INVENTION

According to some embodiments, provided herein is a method of determining an improved estimate of a true relative abundance of a target analyte in a mixed unknown sample using a nanopore device, comprising applying a voltage across a nanopore in a nanopore device to generate a detectable electronic signature and to induce translocation of charged analytes through said nanopore separately for each of: a control sample comprising a known relative abundance of target analytes to reference analytes, and a mixed unknown sample comprising said target analytes and said reference analytes, wherein the relative abundance of said target analytes in said sample is to be determined; generating a plurality of event signatures generated by translocation of said target analytes or said reference analytes through said nanopore for each sample; identifying a quantity of first event signatures associated with said target analyte and a quantity of second event signatures associated with said reference analyte from said plurality of event signatures to determine a detected relative abundance of first and second event signatures for each sample; and adjusting a detected relative abundance of said first and second event signatures in said mixed unknown sample using the detected relative abundance of said first and second event signatures in said control sample to correct for an error in the detected relative abundance, thereby determining an improved estimate of the true relative abundance of said target analyte in said mixed unknown sample. In some embodiments the sample is a liquid sample.

In some embodiments, the control sample is a target control sample comprising said target analytes, but not said reference analytes. In some embodiments, the control sample is a reference control sample comprising said reference analytes, but not said target analytes.

In some embodiments, the method of determining an improved estimate of a true relative abundance of a target analyte in a mixed unknown sample using a nanopore device further comprises applying a voltage to a nanopore device to induce translocation of charged analytes through a nanopore sensor for a target control sample comprising said target analytes, but not said reference analytes.

In some embodiments, the adjustment of said detected relative abundance of said first and second event signatures in said unknown sample comprises using the detected relative abundance of said first and second event signatures in said target control sample and in said reference control sample to correct for said error in the detected relative abundance. In some embodiments, the error comprises a false positive or a false negative detection error of said target analyte.

In some embodiments, the method of determining an improved estimate of a true relative abundance of a target analyte in a mixed unknown sample using a nanopore device further comprises applying a voltage to a nanopore device to induce translocation of charged analytes through a nanopore sensor for a mixed control sample comprising said target analytes and said reference analytes, wherein the relative abundance of said target analytes and said reference analytes is known.

In some embodiments, the adjustment of said detected relative abundance of said first and second event signatures in said unknown sample comprises using the detected relative abundance of said first and second event signatures in said target control sample, said reference control sample, and said mixed control sample to correct for said error in the detected relative abundance.

In some embodiments, the error comprises a false positive target analyte detection error, a false negative target analyte detection error, a capture rate constant differential between said target analyte and said reference analyte, or any combination thereof.

In some embodiments, the control sample is a mixed control sample comprising said target analytes and said reference analytes, wherein the relative abundance of said target analytes and said reference analytes is known. In some embodiments, the error comprises a capture rate constant differential between said target analyte and said reference analyte.

In some embodiments, the mixed control sample comprises a relative abundance of said target analytes to said reference analytes that differs by no more than a factor of 1.2, a factor of 1.5, a factor of 2, a factor of 5, or a factor of 10 relative to said mixed unknown sample.

In some embodiments, the estimate of the true relative abundance is an estimate of the true ratio of said target analyte to said reference analyte in said mixed unknown sample. In some embodiments, the estimate ($R^*_{mix}$) of the true ratio is determined by $R^*_{mix} = \rho\alpha$, wherein the parameter $\rho$ is an estimate for the ratio that can compensate for a false positive detection error, a false negative detection error, or both, and wherein the parameter $\alpha$ can be used to compensate for a capture rate constant differential between said target analyte and said reference analyte. In some embodiments, the parameter $\alpha$ is an estimate of the ratio of the reference analyte capture rate divided by the target analyte capture rate.

In some embodiments, the estimate of the true relative abundance is an estimate of the true fraction of said target analytes in a population of said reference analytes and said target analytes in said mixed unknown sample. In some embodiments, the estimate of the true fraction ($F^*_{mix}$) is determined by $$F^*_{mix} = \frac{\rho\alpha}{\rho\alpha + 1},$$

wherein the parameter $\rho$ is an estimate for the ratio that can compensate for a false positive detection error, a false negative detection error, or both, and wherein the parameter $\alpha$ can be used to compensate for a capture rate constant differential between said target analyte and said reference analyte. In some embodiments, the parameter $\alpha$ is an estimate of the ratio of the reference analyte capture rate divided by the target analyte capture rate In some embodiments, the parameter $$\rho = \left(\frac{Q_{mix} - Q_{ref}}{Q_{targ} - Q_{mix}}\right), \text{ and } \alpha = \left(\frac{Q_{targ} - Q_{X:Y}}{Q_{X:Y} - Q_{ref}}\right) \times \frac{X}{Y}.$$

In some embodiments, the parameter $Q_{targ}$ is the fraction of said first event signature observed in said target control sample if said control sample is used, or $Q_{targ}=1$ if no target control sample is used. In some embodiments, the parameter $Q_{ref}$ is the fraction of said first event signature observed in said reference control sample if said reference control sample is used, or $Q_{ref}=0$ if no reference control sample is used. In some embodiments, the parameter $Q_{X:Y}$ is the fraction of said first event signature observed in said mixed control sample and wherein is $$\frac{X}{Y}$$

is the known ratio of the target analytes (X) to reference analytes (Y) in the mixed control sample if said control sample is used, or $\alpha=1$ if no mixed control sample is used. In some embodiments, the parameter $Q_{mix}$ is the fraction of said first event signature observed in said mixed unknown sample.

In some embodiments, the unknown or control sample is prepared by nucleic acid amplification. In some embodiments, the unknown or control sample is not prepared by nucleic acid amplification. In some embodiments, the sample is purified to substantially consist of reference and target molecules. In some embodiments, the sample is not purified.

In some embodiments, the quantity or concentration of said reference analytes in said mixed unknown sample are known. In some embodiments, the method of determining an improved estimate of a true relative abundance of a target analyte in a mixed unknown sample using a nanopore device further comprises determining an estimate of the absolute quantity or concentration of said target analytes in said mixed unknown sample using said estimate of the true relative abundance of said target analytes to said reference analytes in said mixed unknown sample and said known quantity or concentration of said reference analytes in said mixed unknown sample.

In some embodiments, the quantity of first event signatures associated with said target analyte and said quantity of second event signatures associated with said reference analyte are identified according to a defined threshold. In some embodiments, the method of determining an improved estimate of a true relative abundance of a target analyte in a mixed unknown sample using a nanopore device further comprises optimizing said threshold to increase accuracy of detection of said reference analytes and/or said target analytes using a Q-test, a support vector machine, or an expectation maximization algorithm. In some embodiments, the support vector machine is trained using electronic signatures from control samples comprising known quantities of target analytes and reference analytes.

In some embodiments, the defined threshold is a function of one or more features of an event signature selected from the group consisting of: an event duration, a maximum $\delta G$, a median $\delta G$, an average $\delta G$, a standard deviation of the event signature, a mean or median of the noise power of the event below 50 Hz, a unique pattern in said event signature, an area of an event, or any combination thereof.

In some embodiments, the adjustment of said detected relative abundance of said first and second event signatures in said mixed unknown sample to correct for said error in the detected relative abundance is performed using a Q-test, a support vector machine, or an expectation maximization algorithm.

In some embodiments, the target analyte and said reference analyte each comprise a polynucleotide. In some embodiments, the target analyte polynucleotide and said reference analyte polynucleotide are of different lengths. In some embodiments, the lengths are different by at least 10 nucleotides, at least 20 nucleotides, at least 50 nucleotides, at least 100 nucleotides, at least 150 nucleotides or at least 200 nucleotides.

In some embodiments, the method of determining an improved estimate of a true relative abundance of a target analyte in a mixed unknown sample using a nanopore device further comprises contacting said control or unknown samples with a first probe bound to a first payload, wherein said first probe is configured to bind specifically to said first analyte. In some embodiments, the method of determining an improved estimate of a true relative abundance of a target analyte in a mixed unknown sample using a nanopore device further comprises contacting said control or unknown samples with a second probe bound to a second payload, wherein said second probe is configured to bind specifically to said second analyte.

In some embodiments, the target analyte is correlated with a genetically modified organism. In some embodiments, the target analyte comprises a marker associated with the presence or absence of cancer in a patient.

Also provided herein is a method of determining a relative quantity of a target analyte in a sample comprising running separately in a nanopore system each of: a first control sample comprising reference analytes and no target analytes, a second control sample comprising target analytes and no reference analytes, a third control sample comprising a known relative abundance of said target analytes and said reference analytes, and an experimental sample comprising an unknown relative abundance of said target analytes and said reference analytes; detecting a quantity of first event signatures associated with a reference analyte and a quantity of second event signatures associated with a target analyte for each sample; and comparing a relative abundance of said quantity of first and second event signatures from said experimental sample with a relative abundance of said quantity of first and second event signatures from each of said first control sample, said second control sample, and said third control sample to determine an estimate of the true relative abundance of said reference analyte and said target analyte in said experimental sample.

In some embodiments, the event signature comprises an electrical signal induced by translocation of said reference analyte through said nanopore.

In some embodiments, the target analyte and said reference analyte each comprise a polynucleotide. In some embodiments, the reference analyte and said target analyte are discriminated by length In some embodiments, the reference analyte and said target analyte are each bound to a sequence-specific probe comprising a payload to facilitate discrimination between said reference analyte and said target analyte in said nanopore device.

In some embodiments, the relative abundance is a fractional amount of said target analyte compared to the total population of the target analyte and the reference analyte in said sample.

Also provided herein is a method of determining a relative abundance of a target analyte in an unknown sample, comprising providing an unknown sample comprising a plurality of reference analytes and a plurality of target analytes; loading said unknown sample into a first chamber of a nanopore device comprising a nanopore disposed between said first chamber and a second chamber; applying a voltage across said nanopore to pass said reference analytes and said target analytes through said nanopore from said first chamber to said second chamber; detecting a number of first electrical signals each associated with the translocation of said reference analyte through the nanopore; detecting a number of second electrical signals each associated with the translocation of said target analyte through the nanopore; and converting a relative abundance of the number of detected first electrical signals and the number of detected second electrical signals to an estimate of the true relative abundance of said target analyte in said unknown sample using a reference value that accounts for at least one error associated with said electrical signal relative abundance.

In some embodiments, the reference value is determined from a fractional abundance of said first electrical signal determined from a mixed control sample comprising a known amount of target analytes and reference analytes. In some embodiments, the reference value is determined from a fractional abundance of said first electrical signal determined from a mixed control sample comprising a known amount of target analytes and reference analytes. In some embodiments, the reference value is determined from a fractional abundance of said first electrical signal determined from a mixed control sample comprising a known amount of target analytes and reference analytes.

In some embodiments, the mixed control sample, said target control sample, or said reference control sample is run in said nanopore device under conditions substantially identical to conditions in said nanopore device during said detection of said first and second electrical signals from said unknown sample.

In some embodiments, the nanopore device comprises a membrane that separates an interior space of the device into a first chamber and a second chamber, wherein said membrane comprises said nanopore, wherein said first chamber and said second chamber are in fluid communication through said nanopore, and wherein said device comprises an electrode in each chamber for applying a voltage across said nanopore. In some embodiments, the electrodes are configured to monitor electrical current through said nanopore. In some embodiments, the electrodes are connected to a power supply.

In some embodiments, the methods provided herein improve the accuracy of an estimate of fractional abundance of a target analyte in a mixed unknown sample by accounting for false positive or false negative detection errors, or a capture rate constant differential between said target analyte and said reference analyte. In some embodiments, a series of controls is run to improve the accuracy of the estimate of fractional abundance, including a reference-only control to account for false positive target analyte detection errors, a target-only control to account for false negative target analyte detection errors, and one or more mixed control samples to account for a capture rate constant differential between the target analyte and the reference analyte.

In some embodiments, the capture rates between the target analyte and the reference analyte in the mixed unknown sample are relatively consistent, such that the mixed control does not need to be used to improve the estimate of the relative abundance. In some embodiments, the relative capture rates between the target analyte and the reference analyte in a mixed sample are known such that a correction term can be applied to data from a mixed unknown sample to compensate for this difference to improve the estimate of fractional abundance without running a mixed control sample. In some embodiments, data from a mixed control sample run under substantially identical nanopore conditions using the same target analyte and reference analyte species as in the mixed unknown sample is used to improve the estimate of the fractional abundance without actually running the mixed control sample as part of the method.

In some embodiments, a threshold value is determined such that a false positive value from the mixed unknown sample is negligible, and a reference-only control does not need to be used to improve the estimate of the relative abundance. In some embodiments, the false positive value from a mixed sample is known such that a correction term can be applied to data from a mixed unknown sample to compensate for a false positive error to improve the estimate of fractional abundance without running a reference-only control sample. In some embodiments, data from a reference-only control sample run under substantially identical nanopore conditions using the same reference analyte species as in the mixed unknown sample is used to improve the estimate of the fractional abundance without actually running the reference-only control as part of the method.

In some embodiments, a threshold value is determined such that a false negative value from the mixed unknown sample is negligible, and a target-only control does not need to be used to improve the estimate of the relative abundance. In some embodiments, the false negative value from a mixed sample is known such that a correction term can be applied to data from a mixed unknown sample to compensate for a false negative error to improve the estimate of fractional abundance without running a target-only control sample. In some embodiments, data from a target-only control sample run under substantially identical nanopore conditions using the same target analyte species as in the mixed unknown sample is used to improve the estimate of the fractional abundance without actually running the target-only control as part of the method.

In some embodiments, provided herein is a method of a determining an estimate of a relative abundance of a target analyte to a reference analyte in a mixed sample, comprising applying a voltage to a nanopore device to induce translocation of charged analytes through a nanopore sensor separately for each of: a mixed control sample comprising a known relative abundance of target analytes to reference analytes, and a mixed unknown sample comprising said target analytes and said reference analytes, wherein the relative abundance of said target analytes to said reference analytes is unknown; detecting a quantity of first event signatures associated with said reference analyte and a quantity of second event signatures associated with a target analyte for each sample; and determining an estimate of the true relative abundance of said target analytes to said reference analytes in said mixed unknown sample by adjusting a detected relative abundance of said first and second event signatures from said mixed unknown sample using the detected relative abundance of said first and second event signatures in said mixed control sample and the true relative abundance of said target analytes to said reference analytes in said mixed control sample.

In some embodiments, provided herein is a method of a determining an estimate of a relative abundance of a target analyte to a reference analyte in a mixed sample, comprising applying a voltage to a nanopore device to induce translocation of charged analytes through a nanopore sensor separately for each of: a target control sample comprising target analytes, but not reference analytes, a reference control sample comprising reference analytes, but not target analytes, and a mixed unknown sample comprising said target analytes and said reference analytes, wherein the relative abundance of said target analytes to said reference analytes is unknown; detecting a quantity of first event signatures associated with said reference analyte and a quantity of second event signatures associated with a target analyte for each sample; and determining an estimate of the true relative abundance of said target analytes to said reference analytes in said mixed unknown sample by adjusting a detected relative abundance of said first and second event signatures in said mixed unknown sample using the detected relative abundance of said first and second event signatures in said target control sample and said reference control sample. In some embodiments, the target control sample provides a correction term for false negative detection of target analytes from said mixed unknown sample. In some embodiments, the reference control sample provides a correction term for false positive detection of target analytes in said mixed unknown sample.

In some embodiments, provided herein is a method of a determining an estimate of a relative abundance of a target analyte to a reference analyte in a mixed sample, comprising applying a voltage to a nanopore device to induce translocation of charged analytes through a nanopore sensor separately for each of: a mixed control sample comprising a known relative abundance of target analytes to reference analytes, a target control sample comprising target analytes, but not reference analytes, a reference control sample comprising reference analytes, but not target analytes, and a mixed unknown sample comprising said target analytes and said reference analytes, wherein the relative abundance of said target analytes to said reference analytes is unknown; detecting a quantity of first event signatures associated with said reference analyte and a quantity of second event signatures associated with a target analyte for each sample; and determining an estimate of the true relative abundance of said target analytes to said reference analytes in said mixed unknown sample by adjusting a detected relative abundance of said first and second event signatures from said mixed unknown sample using the detected relative abundance of said first and second event signatures in said target control sample and said reference control sample, and the detected relative abundance of said first and second event signatures in said mixed control sample and the true relative abundance of said target analytes to said reference analytes in said mixed control sample.

In some embodiments, the method of a determining an estimate of a relative abundance of a target analyte to a reference analyte in a mixed sample further comprises applying a voltage to a nanopore device to induce translocation of charged analytes through a nanopore sensor for a target control sample comprising said target analytes, but not said reference analytes.

In some embodiments, the method of a determining an estimate of a relative abundance of a target analyte to a reference analyte in a mixed sample further comprises applying a voltage to a nanopore device to induce translocation of charged analytes through a nanopore sensor for a reference control sample comprising said reference analytes, but not said target analytes. In some embodiments, determining said estimate of the true relative abundance of said target analytes to said reference analytes in said mixed unknown sample comprises adjusting said detected relative abundance of said first and second event signatures in said mixed unknown sample using the detected relative abundance of said first and second event signatures in said target control sample, said reference control sample, and said mixed control sample and the true relative abundance of said target analytes to said reference analytes in said mixed control sample.

In some embodiments, the mixed control sample comprises a relative abundance of said target analytes to said reference analytes that differs by no more than a factor of 1.2, a factor of 1.5, a factor of 2, a factor of 5, or a factor of 10 relative to said mixed unknown sample.

In some embodiments, the relative abundance comprises the ratio of target analyte:reference analyte. In some embodiments, the estimate of the true ratio ($R^*_{mix}$) of said target analyte to said reference analytes in said mixed unknown sample is determined by $R^*_{mix}=\rho\alpha$, wherein the parameter $\rho$ is an estimate for the ratio that can compensate for a false positive detection error, a false negative detection error, or both, and wherein the parameter $\alpha$ can be used to compensate for a capture rate constant differential between said target analyte and said reference analyte. In some embodiments, the parameter $\alpha$ is an estimate of the ratio of the reference analyte capture rate divided by the target analyte capture rate.

In some embodiments, the relative abundance comprises the fraction of said target analyte in a population of said target analytes and said reference analytes. In some embodiments, the estimate of the true fraction ($F^*_{mix}$) of said target analyte in a population of said reference analytes and said target analytes in said mixed unknown sample is determined by $$F^*_{mix} = \frac{\rho\alpha}{\rho\alpha + 1},$$

wherein the parameter $\rho$ is an estimate for the ratio that can compensate for a false positive detection error, a false negative detection error, or both, and wherein the parameter $\alpha$ can be used to compensate for a capture rate constant differential between said target analyte and said reference analyte. In some embodiments, the parameter $\alpha$ is an estimate of the ratio of the reference analyte capture rate divided by the target analyte capture rate.

In some embodiments, provided herein is a kit comprising a control sample comprising a target analyte and a reference analyte at a known relative abundance; and instructions for use to run said control sample and an unknown sample comprising said reference analyte and said target analyte in a nanopore device to determine a relative abundance of said reference analyte and said target analyte in said unknown sample.

In some embodiments, provided herein is a kit comprising a first control sample comprising a target analyte, wherein said first control sample does not contain a reference analyte; a second control sample comprising said reference analyte, wherein said second control sample does not contain said target analyte; a third control sample comprising said target analyte and said reference analyte at a known relative abundance; and instructions for use to run said first control sample, said second control sample, said third control sample and an unknown sample comprising said reference analyte and said target analyte separately in a nanopore device to determine a relative abundance of said reference analyte and said target analyte in said unknown sample.

In some embodiments, provided herein is a computer-implemented method of determining an estimate of a true fractional abundance of a target analyte in a sample, comprising: obtaining data from a nanopore sensor from at least one of a reference analyte control or a target analyte control, wherein said data comprises a plurality of event signatures from target analytes or reference analytes translocating through said nanopore; identifying one or more features of event signatures to differentiate those correlated with target analytes and those correlated with reference analytes; training said support vector machine to identify an optimized threshold to distinguish said first events from said second events and to generate an estimate of the true relative abundance of said reference analytes and said target analytes in a sample, wherein said training comprises use of a control selected from the group consisting of a reference control sample, a target control sample, and a mixed control sample, and wherein training comprises validation using known mixed samples; and using said trained support vector to determine a fractional abundance of target analytes in a sample from events recorded on a nanopore device from a mixed sample.

In some embodiments, provided herein is a computer-implemented method of determining an estimate of a true fractional abundance of a target analyte in a sample, comprising: obtaining a set of data from a nanopore device, said data comprising event signatures from at least one control sample and at least one unknown sample; identifying a set of features to use for generating a threshold to discriminate first event signatures correlated with said target analytes from second event signatures correlated with said reference analytes; and estimating a true value of a fractional abundance in said unknown sample using a trained support vector machine.

BRIEF DESCRIPTION OF THE DRAWINGS

The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead placed upon illustrating the principles of various embodiments of the invention.

DETAILED DESCRIPTION

Figure 1A:
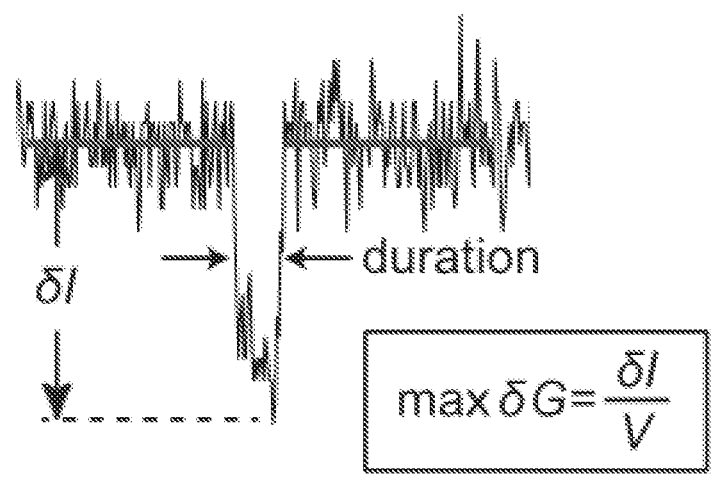
FIG. 1A shows a typical electronic signature of a single-molecule event caused by a dsDNA passing through a nanopore, which a characteristic duration of translocation and decrease in current during translocation.

The details of various embodiments of the invention are set forth in the description below. Other features, objects, and advantages of the invention will be apparent from the description and the drawings, and from the claims.

Definitions

Throughout this application, the text refers to various embodiments of the present nutrients, compositions, and methods. The various embodiments described are meant to provide a variety of illustrative examples and should not be construed as descriptions of alternative species. Rather it should be noted that the descriptions of various embodiments provided herein may be of overlapping scope. The embodiments discussed herein are merely illustrative and are not meant to limit the scope of the present invention.

Also throughout this disclosure, various publications, patents and published patent specifications are referenced by an identifying citation. The disclosures of these publications, patents and published patent specifications are hereby incorporated by reference into the present disclosure to more fully describe the state of the art to which this invention pertains.

As used in the specification and claims, the singular form "a," "an" and "the" include plural references unless the context clearly dictates otherwise. For example, the term "an electrode" includes a plurality of electrodes, including mixtures thereof.

As used herein, the term "comprising" is intended to mean that the devices and methods include the recited components or steps, but not excluding others. "Consisting essentially of" when used to define devices and methods, shall mean excluding other components or steps of any essential significance to the combination. "Consisting of" shall mean excluding other components or steps. Embodiments defined by each of these transition terms are within the scope of this invention.

All numerical designations, e.g., distance, size, temperature, time, voltage and concentration, including ranges, are approximations which are intended to encompass ordinary experimental variation in measurement of the parameters, and that variations are intended to be within the scope of the described embodiment. It is to be understood, although not always explicitly stated that all numerical designations are preceded by the term "about". It also is to be understood, although not always explicitly stated, that the components described herein are merely exemplary and that equivalents of such are known in the art.

As used herein the term "analyte" refers to any molecule, compound, complex, or other entity whose presence can be detected using a nanopore sensor to facilitate determination of a relative abundance of an analyte in the pore. When referring to target or reference analytes, the term target or reference molecule may be used interchangeably.

As used herein, the term "target analyte" refers to a molecule or complex of interest in a sample. In some embodiments, the target analyte comprises portion of a polynucleotide having a sequence of nucleic acids of interest. The target analyte can be specifically targeted for binding by a probe to facilitate detection of the target analyte in a nanopore sensor, as described herein.

As used herein, the term "reference analyte" refers to a molecule or complex of interest in a sample, whose abundance is used as a relative measure of quantification for the target analyte. In some embodiments, the reference analyte comprises portion of a polynucleotide having a sequence of nucleic acids of interest. The reference analyte can be specifically targeted for binding by a probe to facilitate detection of the target analyte in a nanopore sensor, as described herein.

As used herein, the term "specific binding" or "bind specifically" refers to the targeted binding of a probe to a target analyte or a reference analyte.

As used herein, the term "probe" refers to a molecule that binds specifically to a target analyte or to a fragment thereof. In some embodiments, the probe comprises a payload molecule configured to affect the electronic signature generated upon translocation of a complex comprising a target or reference analyte bound to a probe-payload molecule or complex. In some embodiments, the probe comprises a payload molecule binding moiety adapted to bind to a payload molecule.

As used herein, the term "payload molecule" refers to a molecule with physical dimensions that facilitate generation of a unique electrical signal when captured in a nanopore within a correlated range of dimensions. A payload molecule may be bound to a target analyte or a reference analyte to facilitate detection of the target analyte or reference analyte in a nanopore device. In some embodiments, the payload molecule may also be charged to act as a driver molecule. In some embodiments, the payload molecule comprises a probe binding moiety capable of specifically binding a probe molecule, which probe binds specifically to the target analyte or the reference analyte.

The term "nanopore" (or, just "pore") as used herein refers to a single nano-scale opening in a membrane that separates two volumes. The pore can be a protein channel inserted in a lipid bilayer membrane, for example, or can be engineered by drilling or etching or using a voltage-pulse method through a thin solid-state substrate, such as silicon nitride or silicon dioxide or graphene or layers of combinations of these or other materials. Geometrically, the pore has dimensions no smaller than 0.1 nm in diameter and no bigger than 1 micron in diameter; the length of the pore is governed by the membrane thickness, which can be sub-nanometer thickness, or up to 1 micron or more in thickness. For membranes thicker than a few hundred nanometers, the nanopore may be referred to as a "nano channel."

As used here, the term "nanopore instrument" or "nanopore device" refers to a device that combines one or more nanopores (in parallel or in series) with circuitry for sensing single molecule events. Each nanopore within the nanopore device, including its chambers and electrodes used to facilitate sensing with that nanopore, is referred to herein as a nanopore sensor. Specifically, nanopore instruments use a sensitive voltage-clamp amplifier to apply a specified voltage across the pore or pores while measuring the ionic current through the pore(s). When a single charged molecule such as a double-stranded DNA (dsDNA) is captured and driven through the pore by electrophoresis, the measured current shifts, indicating a capture event (i.e., the translocation of a molecule through the nanopore, or the capture of a molecule in the nanopore), and the shift amount (in current amplitude) and duration of the event are used to characterize the molecule captured in the nanopore. After recording many events during an experiment, distributions of the events are analyzed to characterize the corresponding molecule according to its shift amount (i.e., its current signature). In this way, nanopores provide a simple, label-free, purely electrical single-molecule method for biomolecular sensing.

As used herein, the term "electrical signal" encompasses a series of data collected on current, impedance/resistance, or voltage over time depending on configuration of the electronic circuitry. Conventionally, current is measured in a "voltage clamp" configuration; voltage is measured in a "current clamp" configuration, and resistance measurements can be derived in either configuration using Ohm's law V=IR. Impedance can also be generated by measured from current or voltage data collected from the nanopore device. Types of electrical signals referenced herein include current signatures and current impedance signatures, although various other electrical signals may be used to detect particles in a nanopore.

As used herein, the term "event" refers to a translocation of a detectable molecule or molecular complex through the nanopore and its associated measurement via an electrical signal, e.g., change in current through the nanopore over time. It can be defined by its current, change in current from baseline open channel, duration, and/or other characteristics of detection of the molecule in the nanopore. A plurality of events with similar characteristics is indicative of a population of molecules or complexes that are identical or have similar characteristics (e.g., bulk, charge).

As used herein, an "area" of an event refers to the absolute value of the duration of an event (i.e., the duration the current deviates from an open channel current signal) multiplied by the average change in current from the open channel over the duration of the event (i.e., pA*ms).

As used herein, the term "relative abundance" refers to an amount of an item relative to the total number of related items in a group. For example, in the context of a target analyte in a sample, a relative abundance of the target analyte refers to an amount of a target analyte present in a sample as compared to a reference analyte. This can be represented as a fractional abundance, e.g., the percentage of target analyte in a sample compared to the total population of target analytes and reference analytes. The relative abundance can also be represented as a ratio of, e.g., target analytes:reference analytes. In reference to an electronic signature, a relative abundance of a group of electronic signatures can refer to an amount of a first electronic signature correlated with a target analyte as compared to an amount of a second electronic signature correlated with a reference analyte. To distinguish between the actual relative abundance of a target analyte in a sample (i.e., previously measured or prepared to have a known relative abundance) and a relative abundance determined according to the methods provided herein, we often refer to the actual relative abundance as the "true relative abundance," and the relative abundance determined by the methods described herein as an "estimate of the true relative abundance."

As used herein, the term "control sample" refers to a sample containing a known relative abundance of target analyte to reference analyte. Control samples, such as reference control samples, target control samples, and mixed control samples are used herein to improve the accuracy of the estimate of a fractional abundance in an unknown sample. In some embodiments, control samples comprise target analytes, reference analytes, or both.

As used herein, the term "unknown sample" or an "unknown mixed sample" or a "mixed unknown sample" refers to a sample containing a relative abundance of reference analyte that is unknown. A relative abundance of a reference analyte is considered to be unknown if the relative abundance is to be determined by the method provided herein, even if some value of an estimate is already known.

For some unknown samples, a quantity or concentration of a reference analyte in the sample is known.

As used herein, the term "known sample" refers to a sample containing a known relative abundance of target analyte to reference analyte, and is used to train, validate or provide an estimate of an accuracy a fractional abundance estimation model or feature of the model, such as a threshold.

Introduction/Overview

The invention provided herein, in some embodiments, is a method for determining an estimate of the true relative abundance (e.g., a fractional amount or a ratio) of a target analyte relative to a reference analyte present in a sample. This method takes advantage of a nanopore single molecule counter (i.e., a nanopore device) to detect and discriminate between target analytes and reference analytes in a sample.

The use of raw electronic event signatures correlated with target analytes and reference analytes to determine an estimate for a relative abundance of the target analyte in a sample may be inaccurate for several reasons, including false positive detection errors, false negative detection errors, and errors associated with a capture rate constant differential between target analyte and reference analyte in a mixed sample. Herein, we provide, according to some embodiments, methods to improve the accuracy of estimating the true fractional abundance of reference and target analytes in a sample. In some embodiments, these methods entail the use of control samples specifically designed to correct for one or more errors associated with electronic signal detection in a mixed sample. When the mixed sample comprises a known quantity or concentration of reference analytes, the improved estimate of relative abundance can be used to provide an improved estimate of the true quantity or concentration of target analytes in a sample.

In some embodiments, the methods provided herein improve the accuracy of an estimate of fractional abundance of a target analyte in a mixed unknown sample by accounting for false positive or false negative detection errors, or a capture rate constant differential between said target analyte and said reference analyte. In some embodiments, a series of controls is run to improve the accuracy of the estimate of fractional abundance, including a reference-only control to account for false positive target analyte detection errors, a target-only control to account for false negative target analyte detection errors, and one or more mixed control samples to account for a capture rate constant differential between the target analyte and the reference analyte.

In some embodiments, the capture rates between the target analyte and the reference analyte in the mixed unknown sample are relatively consistent, such that the mixed control does not need to be used to improve the estimate of the relative abundance. In some embodiments, the relative capture rates between the target analyte and the reference analyte in a mixed sample are known such that a correction term can be applied to data from a mixed unknown sample to compensate for this difference to improve the estimate of fractional abundance without running a mixed control sample. In some embodiments, data from a mixed control sample run under substantially identical nanopore conditions using the same target analyte and reference analyte species as in the mixed unknown sample is used to improve the estimate of the fractional abundance without actually running the mixed control sample as part of the method.

In some embodiments, a threshold value is determined such that a false positive value from the mixed unknown sample is negligible, and a reference-only control does not need to be used to improve the estimate of the relative abundance. In some embodiments, the false positive value from a mixed sample is known such that a correction term can be applied to data from a mixed unknown sample to compensate for a false positive error to improve the estimate of fractional abundance without running a reference-only control sample. In some embodiments, data from a reference-only control sample run under substantially identical nanopore conditions using the same reference analyte species as in the mixed unknown sample is used to improve the estimate of the fractional abundance without actually running the reference-only control as part of the method.

In some embodiments, a threshold value is determined such that a false negative value from the mixed unknown sample is negligible, and a target-only control does not need to be used to improve the estimate of the relative abundance. In some embodiments, the false negative value from a mixed sample is known such that a correction term can be applied to data from a mixed unknown sample to compensate for a false negative error to improve the estimate of fractional abundance without running a target-only control sample. In some embodiments, data from a target-only control sample run under substantially identical nanopore conditions using the same target analyte species as in the mixed unknown sample is used to improve the estimate of the fractional abundance without actually running the target-only control as part of the method.

Sample Uses

Determining the fractional amount of a target sequence within a nucleic acid fragment, compared to a reference nucleic acid molecule, has many applications.

In one example use case, we use the methods herein to determine the fractional amount of a transgenic sequence of a genetically modified organism (GMO) to the non-GMO reference sequence within genomic DNA, obtained from a collection of seeds for example. This determination is important for regulatory and economic reasons. The buyer and sellers of seeds with the desired trait require precise and accurate knowledge of the fraction of seeds comprising the desired trait in order for the pricing and transaction to be fair.

Therefore, in some embodiments, the methods provided herein provide % GMO content determination from aggregate seed, grain, flour, and feed presumed to contain between 1-100% GMO content. Seed developers, growers, and regulatory agencies want precise measures and the ability to resolve 10% differences (1.1-fold) in GMO content. % GMO defined as 100× (GMO event copy number)/(taxon-specific genome reference copy number).

As another example use case, we use the methods described herein to monitor the relative abundance of polynucleotide sequences comprising point mutations to non-mutant (wildtype) sequences within cell-free circulating DNA from a blood or urine sample. Relative abundance of point mutations at specific genomic loci have been correlated with cancer types and treatment outcomes. A determination of mutant relative abundance to non-mutant sequences can be used to guide diagnoses, therapies, and disease progression monitoring. Although it can take weeks for tumor imaging results to reveal a shrinking/growing mass, the methods described herein allow rapid identification of the relative abundance of mutation markers permits efficient and frequent testing (e.g., daily) by using easily accessible sample types. Critically, such technology could more effectively reveal therapy response by providing more time points of the disease dynamics, while also permitting early detection of relapse.

In some embodiments, the methods provided herein provide copy number variation determination (CNV) in hereditary cancer screening assays. Copy number variation (CNV) testing for hereditary cancer pre-disposition. Goal is to detecting deletions or duplications of gene regulatory elements at <1.5-fold difference from reference. 10% differences in the copy number (1.1 fold) of the BRCA1 gene for example, may warrant clinical action.

Nanopore Detection

A nanopore is formed in a solid-state silicon based substrate, and single molecule experiments are performed by applying a voltage across the pore in a buffered electrolytic solution.

Figure 1B:
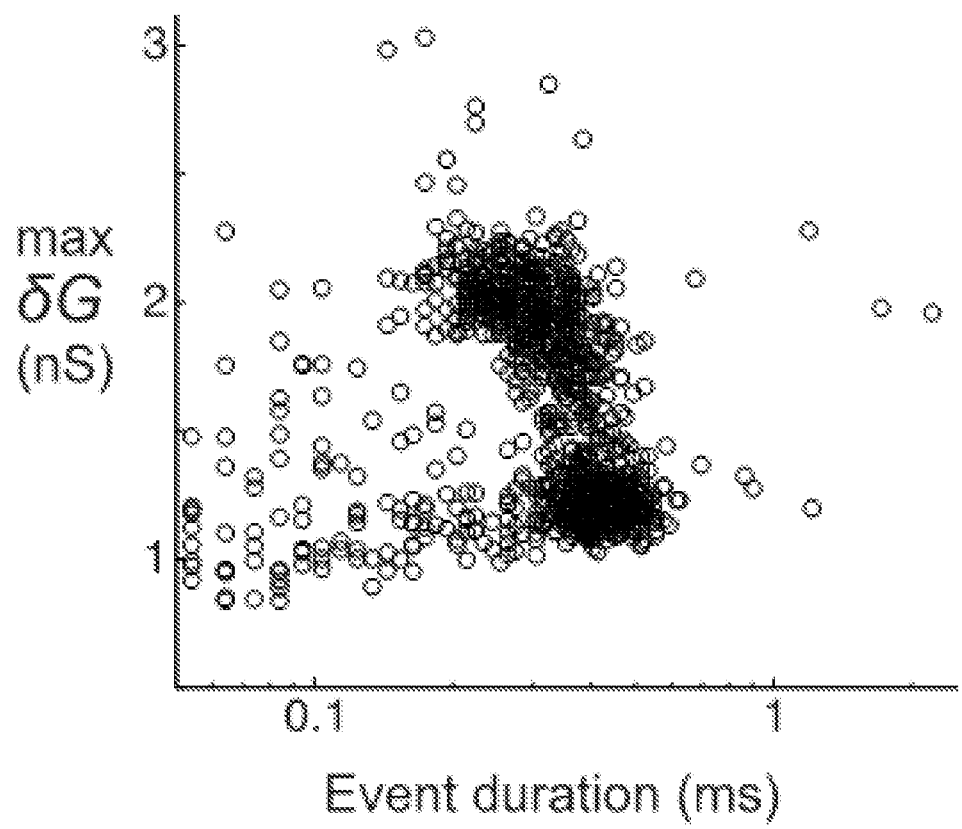
FIG. 1B shows an all-event scatter plot of max $\delta G$ versus duration for 5.6 kb dsDNA recorded in a 22 nm diameter nanopore.

FIG. 1A shows a typical single-molecule event caused by a dsDNA passing through a nanopore. Events are quantitated by duration width and maximum conductance depth, max $\delta G$. The max $\delta G$ is the current attenuation $\delta I$ divided by applied voltage V. FIG. 1B shows an all-event scatter plot of max $\delta G$ versus duration for 1072 events of 5.6 kb dsDNA recorded in 5 minutes with a 22 nm diameter nanopore (V=100 mV, 1 nM DNA, 1 M LiCl, 10 mM Tris, 1 mM EDTA, pH=8.8).

Besides max $\delta G$ and duration, other features of the event profile that can be quantitated are: the mean $\delta G$, the median $\delta G$, the standard deviation of the event signal, and other higher order features. Another useful feature is the absolute value of the integrated area of the event, which can be computed as the mean $\delta G$ times the duration (Storm, A J, J H Chen, H W Zandbergen, and C Dekker. "Translocation of Double-Strand DNA Through a Silicon Oxide Nanopore." Physical Review E 71, no. 5 (May 2005): 051903, doi: 10.1103/PhysRevE.71.051903). The integrated area, or just "area", is also known as the electric charge deficit (Fologea, Daniel, Marc Gershow, Bradley Ledden, David S McNabb, Jene A Golovchenko, and Jiali Li. "Detecting Single Stranded DNA with a Solid State Nanopore." *Nano Letters* 5, no. 10 (October 2005): 1905-9. doi: 10.1021/n1051199m).

For dsDNA that is long enough to pass through the nanopore in a folded state (>700 bp), the events can display more than one amplitude. FIG. 1B is an example of this, with fully folded events displaying larger max $\delta G$ values and shorter durations, and unfolded events displaying longer durations and shallower max $\delta G$ values. Partially folded events display both amplitude levels within the event, starting with the deeper level and finishing with the shallower level, and having a total duration width that is in between that of unfolded and fully folded events. While the $\delta G$ and duration distributions show a mixture of modes for dsDNA that can fold, the event area has a single mode distribution for dsDNA, regardless of whether or not the DNA is long enough to fold when passing through the nanopore.

Discrimination between target analytes and reference analytes using a nanopore is based on the detection of a sufficiently different event signature upon translocation of each through the nanopore to enable reliable and sensitive detection. The differences in the average event signatures can be based on signature duration, changes in current, features within the signature, or other distinguishable features and combinations thereof. The features used are the basis for the determination of a threshold which acts as a method of identifying event signatures correlated to reference analytes and target analytes to be used for fractional abundance determination described herein.

In some embodiments, the target and reference fragments are sufficiently different length dsDNA molecules to produce different nanopore event durations.

In some embodiments, both target and reference analytes are dsDNA, and the feature that creates the distinct event types could be a difference in length of the target and reference analytes. In such embodiments, the difference in target and reference event areas, which are created by the difference in length of the target and reference analytes, are used to distinguish the target and reference event signatures (i.e., event profiles).

The event area distribution for dsDNA has a single mode. This makes area a useful event feature for classifying events as being the target type or the reference type, when the target and reference analytes are dsDNA of sufficiently different lengths. To generate sufficiently different area distributions, the lengths should be different by at least 100 bp for nanopores larger than 20 nm in diameter. For smaller nanopores 1-20 nm in diameter, e.g., formed by controlled dielectric breakdown (Yanagi, Itaru, Rena Akahori, Toshiyuki Hatano, and Ken-ichi Takeda. "Fabricating Nanopores with Diameters of Sub-1 Nm to 3 Nm Using Multilevel Pulse-Voltage Injection." Scientific Reports 4 (2014): 5000 doi: 10.1038/srep05000), the dsDNA for the target and reference should be at least 20 bp different in length.

There is no apparent upper limit on how different the dsDNA lengths can be for the target and reference molecules.

Figure 2A:
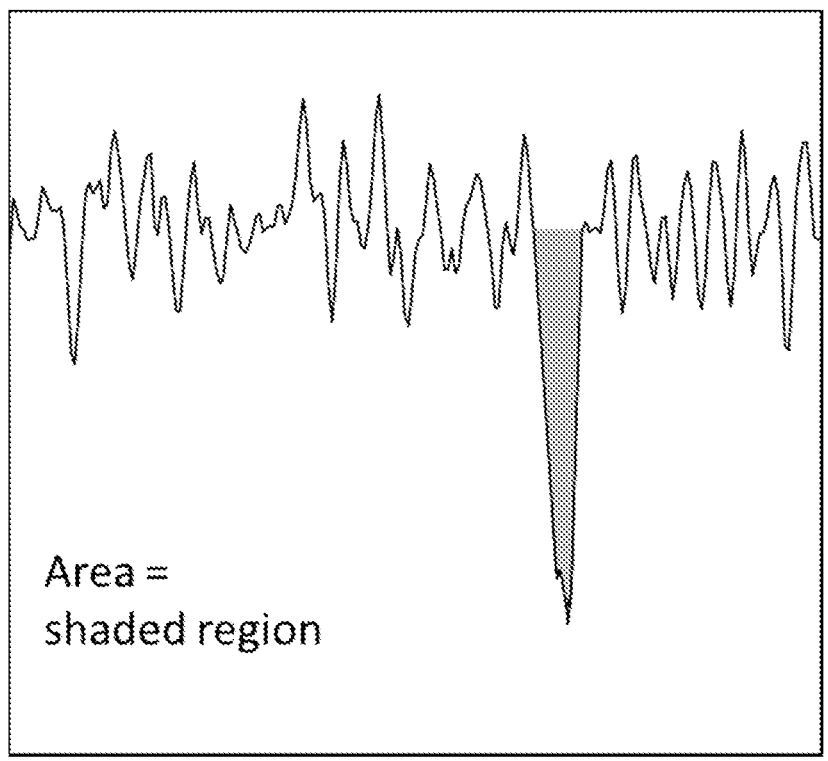
FIG. 2A shows a typical event when a 727 bp DNA goes through a 25 nm diameter solid-state nanopore at 100 mV in 1 M LiCl. The vent area is shaded.
Figure 2B:
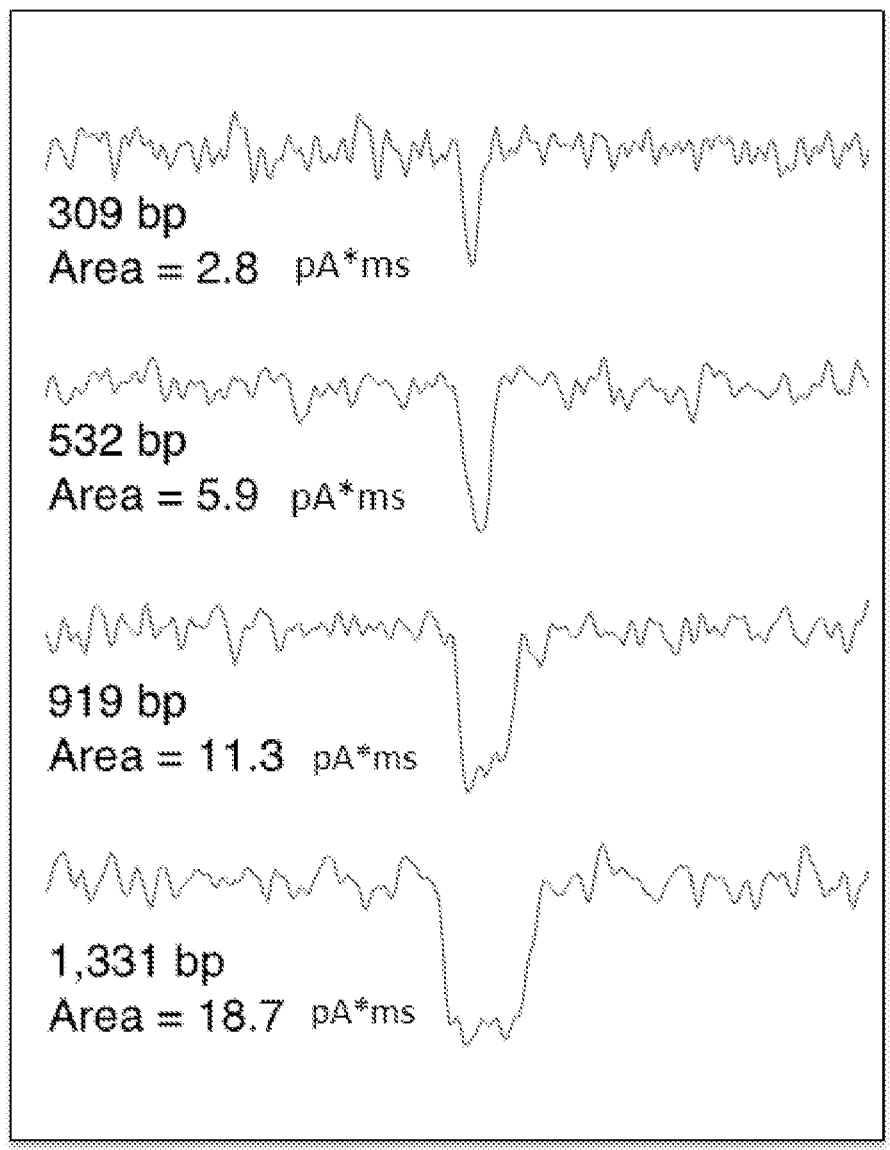
FIG. 2B illustrates an increase in event duration with increased dsDNA length, while event depth is conserved.
Figure 2C:
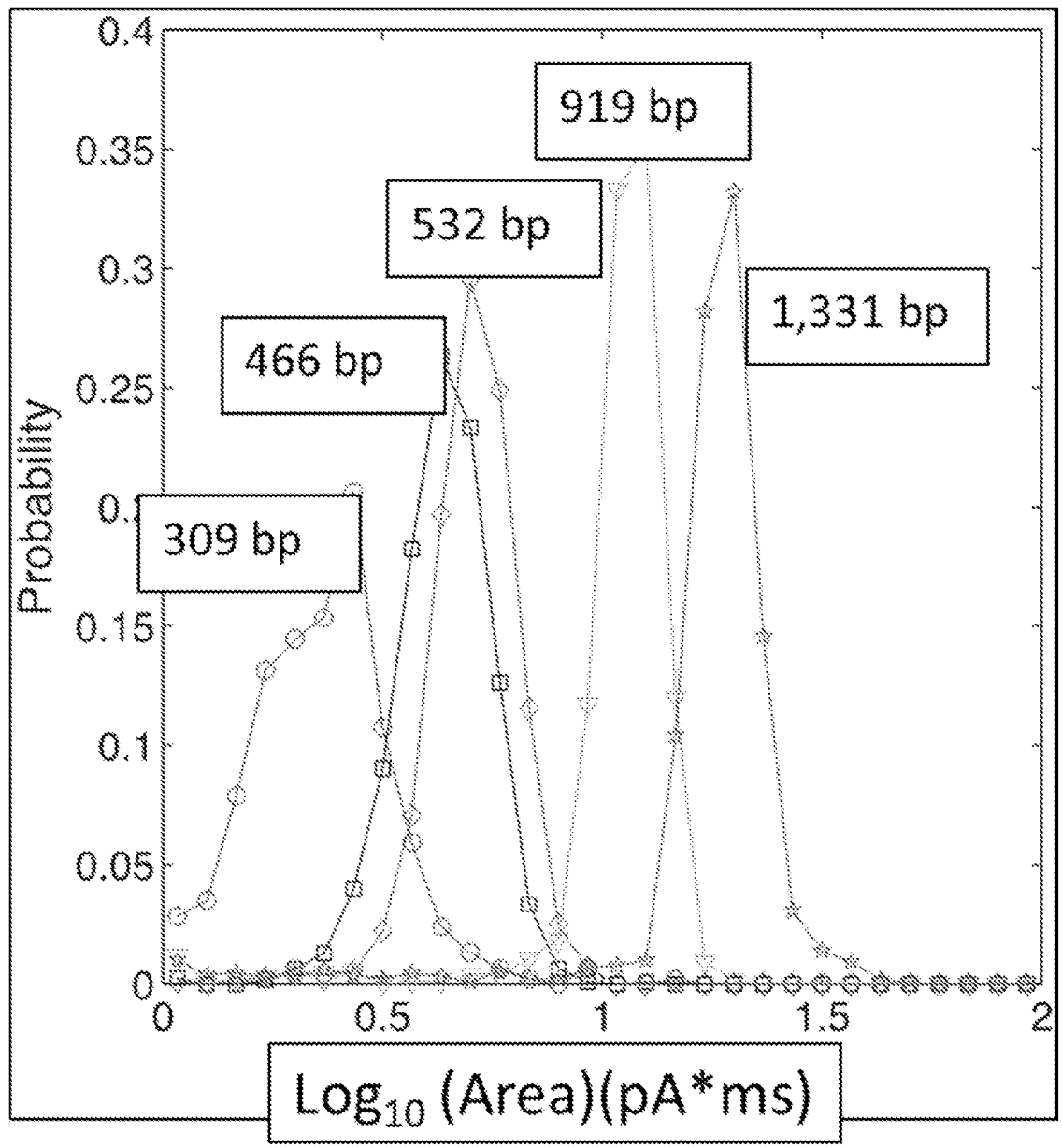
FIG. 2C shows a plot of the distribution of the $\log_{10}$ of the area of all events recorded for dsDNA at each length shown.

FIG. 2A shows a typical event when a 727 bp DNA goes through a 25 nm diameter solid-state nanopore at 100 mV in 1 M LiCl. The event area is shown as the shaded region. FIG. 2B shows how event area increases with dsDNA length. Primarily, it is event duration that is increasing while event depth remains conserved, and event area (mean depth times duration) captures this length-dependent increase since it is proportional to duration. FIG. 2C shows the distribution of the log-base-10 of the area (pA*ms) of all events recorded for each DNA length shown, run sequentially on the same nanopore. The distribution of log-base-10 of event areas is approximately normal (Gaussian). As the DNA increases in length, the mean of the distribution increases.

To create target-sequencing comprising dsDNA and reference-sequence comprising dsDNA, with the two dsDNA lengths at least 300 bp in length, at most 100,000 bp in length. In some embodiments, the target and reference dsDNA analytes have a difference in length of at least 10 bp, 20 bp, 30 bp, 40 bp, 50 bp, 60 bp, 70 bp, 80 bp, 90 bp 100 bp, 150 bp, 200 bp, or 300 bp. In general, an increased difference in length between the target and reference dsDNA analytes facilitates a greater sensitivity and specificity of determination of event signatures correlated with the target and reference analytes, when discriminating by size, which improves the estimation of the relative abundance in the sample.

In some embodiments, specifying the properties of polynucleotide fragments excised from genomic DNA (gDNA) is a portion of the workflow for fractional abundance determination. These fragment specifications can include, e.g., their sequences, lengths, and secondary structures. In some embodiments, the fragment specifications enhance the capture and detection of specific sequences by the nanopore device.

In some embodiments, the target and reference fragments are bound to different payload molecules, such that the target/payload and reference payload molecules produce sufficiently different nanopore event signatures. In some embodiments, the different event signatures are a combination of event duration, event maximum depth, event mean depth, and/or other event properties.

In some embodiments, the target and reference analytes are discriminated by sequence specific payloads that, when each molecule or complex type (target-payload, reference-payload) passes through the pore, a unique nanopore event signature is generated. Methods for using probes bound to payloads that bind to each molecule type to facilitate discrimination are described in International Publication No. WO/2015/171169, "Target Detection with a Nanopore," International Publication No. WO/2014/182634, "A Method of Biological Target Detection Using a Nanopore and a Fusion Protein Binding Agent," International Publication No. WO/2016/049657, "Target Sequence Detection by Nanopore Sensing of Synthetic Probes," International Publication No. WO/2016/126746, "Nanopore Detection of Target Polynucleotides from Sample Background," and International Publication No. WO/2017/173392, "Nanopore Discrimination of Target Polynucleotides from Sample Background by Fragmentation and Payload Binding," each of which are incorporated by reference herein in its entirety.

In some embodiments, target and/or reference analytes are dsDNA, with unique payload-bound PNAs invading each dsDNA type (target and reference) to create the two macromolecule types to be detected with the nanopore. In some embodiments, target and/or reference analytes are single-stranded nucleic acid (ssNA), including DNA or RNA. A payload-bound complementary nucleic acid (e.g., LNA) hybridizes to a region on the ssNA and one or more flanking primers hybridize to the other regions of the ssNA, to create a double-stranded molecule with payload bound, and the payloads are unique for the target and the reference in order to create the unique target and reference event profiles.

Fractional Abundance Framework

In some embodiments, the fractional abundance framework involves: 1) designing and applying biochemistry methods to convert sample material into the nanopore sensing formats, for both target analyte and reference types; 2) applying a specific nanopore experiment protocol; and 3) applying analytical methods to generate a quantitative estimate for the relative abundance of target to reference analytes. This section is focused on part 1 of the framework.

Sample Preparation for Nanopore Detection

A molecule comprising the target sequence (termed the "target analyte" or "target molecule") and a molecule comprising the reference sequence (termed a "reference analyte" or "reference molecule") may be physically similar: for example target and reference molecules may be of similar molecular weights, or polynucleotide lengths, and may differ by only single nucleotides. The goal of the biochemistry methods is to render target and reference molecules without bias to produce distinct "target" or "reference" event profiles upon translocation through the nanopore. In this way, the target:reference mixture measured on the nanopore is representative of the target:reference concentration ratio in the sample.

In some uses cases it may be advantageous to add polynucleotide sequence to target, reference, or both molecules to generate distinct event profiles. For example, the majority of DNA fragments obtained from the cell-free circulating DNA fraction of blood or urine are uniformly short 150-200 bp in length. Adding polynucleotide sequences by common methods including PCR, ligation, and direct oligonucleotide hybridization allows flexibility to maximize nanopore event distinction. In other cases, hybridization of chemically modified oligonucleotide probes carrying covalently bound polymer payloads are used to alter target or reference analyte charge and molecular weight without affecting polynucleotide length. In all cases, the goal is distinct event profiles per target and reference molecule groups.

There are use cases, including the GMO example (fractional amount of soy seeds containing the GMO target sequence), where there is sufficient starting material that enrichment strategies can be used without needed PCR prior to nanopore sensing. There are other cases, including liquid biopsy, where PCR is required as part of enrichments, since a blood or urine sample could contain <10 target sequences per mL of fluid. The proposed method is agnostic to the sample prep requirements, including sample collection, purification and concentration of the target and reference. The nanopore measurement and subsequent fractional abundance quantitation can be implemented provided the target and reference are sufficiently enriched (>10 pM) compared to background (<1 pM), and provided the target and reference analytes produce electrical event signatures that can be distinguished from one another and from background, where present.

In some embodiments, target or reference analytes include polynucleotide sequences (including double and single stranded DNAs, RNAs, and synthetic polynucleotides) 20 nt-100,000 nt in length. In some embodiments, the polynucleotide comprising the target sequence is derived from organismal gDNA including from plants, humans, animals, insects, bacteria or viruses. In some embodiments, target polynucleotide sequences are derived from exogenous, non-genomic sequences including double or single-stranded RNA or DNA from sources including plasmid, BAC, linear sequence-verified gene blocks, expression cassettes.

In some embodiments, we provide an enrichment specific to the fractional abundance (e.g., copy number variation) detection by the nanopore device. In some embodiments, we use site-directed fragmentation methods to prepare the sample for detection by the nanopore. In some embodiments, the methods of detection provided herein include upstream fragmentation of polynucleotides fragmentation of nucleic acid samples, for example, gDNA to sizes 20-100,000 nt or base pairs in length In some embodiments, the nucleic acid is fragmented sequence-specifically using restriction enzymes, or by using site-directed nucleases including Cas9/sgRNA, TALENS, zinc finger proteins/nucleases, or another fragmentation method known in the art.

In some embodiments, target or reference analyte enrichment is performed using positive and negative size selection to retain, discard, and elute target fragment sizes. For example, low ratio of SPRI beads:DNA (0.6) in the presence of PEGs to retain and discard high molecular weight polynucleotide species (for example >8,000 bp DNA), followed by SPRI beads:DNA (1.5:1) to bind, wash and elute fragment sizes (2000-8000 bp for example). In some embodiments, target or reference nucleic acids can undergo nucleic acid amplification to facilitate detection in a nanopore.

Nanopore Detection

The fractional abundance framework involves: 1) designing and applying biochemistry methods to convert sample material into the nanopore sensing formats, for both target analyte and reference types; 2) applying a specific nanopore experiment protocol; and 3) applying mathematical methods to generate a quantitative estimate for the fractional amount of target to reference (target:reference) analytes. This section is focused on part 2, experiment protocol.

Described herein are iterations of samples to be run in a nanopore to provide an improved estimate of the true relative abundance of target analytes in a mixed unknown sample. In some embodiments, the target analyte and the reference analyte are prepared to ensure reliable discrimination between each species using a nanopore sensor. In some embodiments, the characteristics of a fragment comprising a target sequence (i.e., the "target fragment") and the characteristics of a fragment comprising the reference sequence (i.e., the "reference fragment") are chosen such that the two fragments produce nanopore event signatures that can be differentiated by one or more signal properties.

In some embodiments, one or more control mixtures (i.e., control samples) is used to calibrate the estimate of the fractional amount of target to reference in an unknown mixture. In some embodiments, the calibration compensates for difference in nanopore capture efficiency between the target and the reference molecule types.

In some embodiments, an unknown mixture of target and reference analytes is measured on the nanopore, and the fraction abundance of target to reference is mathematically quantitated. In some embodiments, more than one unknown mixture of target and reference molecule types, derived from the same sample, is measured sequentially on the same nanopore. In some embodiments, more than one unknown mixture of target and reference molecule types, derived from the same sample, is measured in parallel on different nanopores.

In some embodiments, one or more controls, including 100% target alone, 100% reference alone, and known mixtures of target and reference molecules, are measured on the nanopore, prior to and/or after the unknown mixtures.

In some embodiments, the experiment protocol involves sequentially running one or more controls on the nanopore, before or after, or before and after, running the unknown mixture on the nanopore. The controls can be made of 100% target analytes, or 100% reference analytes, and these are termed "isolated controls." The controls can also be any known mixture of target and reference analytes, referred to as "mixture controls" or "control mixtures." The control mixture could be a 1:1 ratio of target:reference analytes, or any other ratio of target:reference analytes from 0.01:1 to 100:1, or any ratio less than 0.01:1 (e.g., 0.001:1) or any ratio greater than 100:1 (e.g., 1000:1) of target:reference analytes. One or more controls can be run more than once. The controls (isolated and mixtures) and unknown mixture can be run in any order sequentially on the same nanopore. In between controls and unknown samples, the fluidic channel (i.e., chamber) from which the nanopore captures molecules is flushed.

In some embodiments, no controls are run, and only the unknown mixture is run, and compared to a reference table established by running controls in separate prior experiments, i.e., the controls are not run at the point of use.

In some embodiments, one or more fluidically isolated channels and nanopore sensors are measuring controls in parallel with a one or more fluidically isolated channels and nanopore sensors measuring unknowns. More than one nanopore could have access to each fluidic channel. In parallelized implementations, no flushing may be necessary, since each pore sees only one reagent set, i.e., a control (isolated or mixture) or an unknown (from a set of 1 or more unknowns).

In some embodiments, the ratio of the reference analyte to the target analyte in the control mixture concentration is near the anticipated ratio of reference analyte to target analyte in the unknown sample, although this may not be known ahead of time.

Any number of unknown mixtures can be sequentially run on the same nanopore, flushing out the prior unknown before each new unknown is added for measurement. This requires that the unknown mixtures are comprised of the same target and reference analyte types, though their ratios cane be the same or different in the different unknowns.

Each recording period should be long enough to detect at least 100 events for each reagent type, and performance improves as more events are recorded, where the improvement is significant when more than 500 events are recorded, and very significant when more than 1000 events are recorded. The recording period for each reagent set can be the same or different. An adaptive scheme can stop recording dynamically when the target number of molecules is detected. We have previously established a method for determining the number of molecules needed to achieve a desired level of confidence (e.g., 95%, 98%, 99%, 99.9%, etc.) that can be applied to any reagent set (control or unknown) in the presented workflow (SI Section 10.2, Morin, Trevor J, Tyler Shropshire, Xu Liu, Kyle Briggs, Cindy Huynh, Vincent Tabard-Cossa, Hongyun Wang, and William B Dunbar. "Nanopore-Based Target Sequence Detection." Edited by Meni Wanunu. PloS One 11, no. 5 (May 5, 2016): e0154426-21. doi:10.1371/journal.pone.0154426).

In some embodiments, an experiment protocol with a single nanopore is to run 1) 100% target for recording period T, 2) flush nanopore chamber, 3) 100% reference for recording period T, 4) flush nanopore chamber, 5) 50:50 target:reference mixture for recording period T, 6) flush nanopore chamber, 7) unknown mixture for recording period T. Recording period T can be 15 sec, 30 sec, 45 sec, 1 min, 5 min, 10 min, or any duration between 1-15 sec or between 10-60 min.

Another common experiment protocol is to run (1)-(7), followed by 8) flush nanopore chamber, 9) repeat 100% target for recording period T, 10) flush nanopore chamber, 11) repeat 100% reference for recording period T, 12) flush nanopore chamber, 13) repeat 50:50 target:reference mixture for recording period T.

Another common experiment protocol is to run (1)-(7), followed by 8) flush nanopore chamber, 9) repeat 50:50 target:reference mixture for recording period T, 10) flush nanopore chamber, 11) repeat 100% reference for recording period T, 12) flush nanopore chamber, 13) repeat 100% target for recording period T.

Still another common experiment protocol is to run 1) a target:reference control mixture ratio suspected to be approximately near to the target:reference ratio in the unknown mixture, for recording period T, 2) flush nanopore chamber, 3) unknown mixture for recording period T.

Still another common experiment protocol is to run 1) a 1:1 target:reference control mixture ratio for recording period T, 2) flush nanopore chamber, 3) unknown mixture for recording period T.

In some embodiments, an experiment protocol with a single nanopore is to run 1) 100% target for recording period T, 2) flush nanopore chamber, 3) 100% reference for recording period T, 4) flush nanopore chamber, 5) unknown mixture for recording period T.

In some embodiments, an experiment protocol with a single nanopore is to run 1) 100% target for recording period T, 3) flush nanopore chamber, 4) unknown mixture for recording period T.

In some embodiments, an experiment protocol with a single nanopore is to run 1) 100% reference for recording period T, 2) flush nanopore chamber, 3) unknown mixture for recording period T.

In some embodiments, an experimental protocol with a single nanopore is to run only the unknown mixture for a recording period T, and to use data from a lookup table or previous data which contains error correction information derived from a 100% reference control sample, a 100% target control sample, a known target:reference control mixture, or any combination thereof, each run under substantially similar conditions to the experimental protocol for the unknown mixture, to provide at least one correction term to the data generated from the recording period T to improve an estimate of a fractional abundance of a target analyte in the unknown mixture.

Upon completion of the experiment protocol, the recorded events from the controls (if run) and the recorded events from the unknown(s) are mathematically analyzed to predict the fraction amount of target to reference in the one or more unknowns.

Fractional Abundance Estimation and Threshold Determination

The fractional abundance framework involves: 1) designing and applying biochemistry methods to convert sample material into the nanopore sensing formats, for both target analyte and reference types; 2) applying a specific nanopore experiment protocol; and 3) applying mathematical methods to generate a quantitative estimate for the fractional amount of target to reference (target:reference) analytes. This section is focused on part 3 of the framework.

In some cases, the estimated concentration ratio $R=[t]/[r]$ of target sequence "t" to reference sequence "r" is quantitated. The percentage transgene, or GMO %, is the ratio R converted to a percentage. In some cases, the estimated fractional amount $F=[t]/([t]+[r])$ of target sequence to total (target plus reference sequence) is quantitated. A simple conversion between the ratio R and the fraction F exists, namely $F=R/(R+1)$ or, equivalently, $R=F/(1-F)$.

The fractional abundance method predicts the relative amount of target to reference, or target to total (sum of target and reference). In some embodiments, a calibrant molecule can be added to determine absolute concentration of either the target or the reference molecule. In some embodiments, a single nanopore event feature is compared between target and reference analyte types for calculating the fractional abundance. In some embodiments, more than one nanopore event feature is compared between target and reference analyte types for calculating the fractional abundance.

There are three methods we have describe herein to improve a threshold determination to discriminate event signatures correlated with target analytes and reference analytes and to correct for errors from the use of event signatures from a nanopore to determine fractional abundance: 1) The Q-test method, 2) the Support Vector Machine (SVM), and 3) the Expectation Maximization Algorithm for Gaussian Mixtures (EMGM) method.

The following general concepts apply to the methods. First, the true ratio of target analytes "t" to reference analytes "r" is denoted $R=[t]/[r]$. The true fraction of target analytes to total (target plus reference) analytes is denoted $F=[t]/([t]+[r])$. A simple conversion between the ratio R and the fraction F is $F=R/(R+1)$ or, equivalently, $R=F/(1-F)$. The true ratio of an unknown mixture is denoted $R_{mix}$ and the true fraction of a mixture is denoted $F_{mix}$. The mathematical method generates estimates for $F_{mix}$ and $R_{mix}$, which are denoted $F^*_{mix}$ and $R^*_{mix}$. The target and reference molecule constructs are designed and created to give distinct nanopore event signatures.

The Q-test Method

The mathematical method first designs a criterion for binning all recorded events into one or two categories, namely, target positive (equivalently, reference negative) or target negative (equivalently, reference positive). The event criterion uses one or more event features. In some embodiments, a single feature is used to create a criterion for binning events. Given the criterion, every event is tagged as being either a target event or a reference event. These are termed "target-tagged" or "reference-tagged."

The fraction of target-tagged events is denoted Q, equal to the number of target-tagged events divided by the total number of events. The fraction of reference-tagged events is 1-Q. The tagged fraction Q is a function of the concentration fraction F above the nanopore, written as Q(F).

The fraction of target-tagged events in a mixture $Q(F_{mix})$ is denoted as $Q_{mix}$; the fraction of target-tagged events in a 100% target control $Q(1)$ is denoted as $Q_{targ}$; the fraction of target-tagged events in a 100% reference control $Q(0)$ is denoted as $Q_{ref}$; the fraction of target-tagged events in a target:reference control mixture is denoted as $Q_{X:Y}$ where X:Y is the ratio of the mixture of target-to-reference in the control mixtures. For fraction $z=X/(X+Y)$, we have $Q(z)=Q_{X:Y}$. In some embodiments, the 1:1 ratio control mixture is preferred with $z=0.5$ and the tagged fraction is written $Q_{1:1}$ or $Q_{50:50}$.

Typically, $Q_{targ}$ is close to 1, with $1-Q_{targ}$ representing the false negative fraction. Typically, $Q_{ref}$ is close to 0, with $Q_{ref}$ representing the false positive fraction. The controls satisfy $Q_{targ} \geq Q_{X:Y} \geq Q_{ref}$ The mixture satisfies $Q_{targ} \geq Q_{mix} \geq Q_{ref}$.

In some embodiments, the target-tagged fractions from controls ($Q_{targ}$, $Q_{ref}$, $Q_{X:Y}$) are run separately and a lookup table is used to reference the values for any new assay that measures $Q_{mix}$. In some embodiments, the ($Q_{targ}$, $Q_{ref}$, $Q_{X:Y}$) are established at the point of use as part of the assay. In some embodiments, the ($Q_{targ}$, $Q_{ref}$) are run separately and a lookup table is used to reference their values, whereas the ($Q_{X:Y}$) value is established at the point of use as part of the assay that measures $Q_{mix}$.

In some embodiments, the target-tagged fractions from controls ($Q_{targ}$, $Q_{ref}$, $Q_{X:Y}$) are run more than once at the point of use, and their values are averaged for subsequent use in the formula below.

The formula for estimate $F^*_{mix}$ for the true fractional amount $F_{mix}$ is given by:

$$F^*_{mix} = \frac{\rho\alpha}{\rho\alpha + 1} \quad \text{(Equation 1)}$$

where $$\rho = \left(\frac{Q_{mix} - Q_{ref}}{Q_{targ} - Q_{mix}}\right), \text{ and } \alpha = \left(\frac{Q_{targ} - Q_{X:Y}}{Q_{X:Y} - Q_{ref}}\right) \times \frac{X}{Y}.$$

The formula for estimate $R^*_{mix}$ for the true ratio $R_{mix}$ is given by:

$$R^*_{mix} = \rho\alpha \quad \text{(Equation 2)}$$

In examples for predicting the fractional amount of a transgene (GMO), the GMO (%) is equal to $R^*_{mix} \times 100(\%)$.

The parameter $\rho$ is an estimate for the ratio that can compensate for a false positive detection error, a false negative detection error, or both. In some embodiments, a value of $Q_{ref}$ can be used to compensate for a false positive error. If no compensation for a false positive error is to be used, $Q_{ref}$ can be set to 0. In some embodiments, a value of $Q_{targ}$ can be used to compensate for a false negative error. If no compensation for a false negative error is to be used, $Q_{targ}$ can be set to 0.

The parameter $\alpha$ is the ratio compensation multiplier. Analytically, the parameter $\alpha$ is the ratio of two capture rate constants. A capture rate constant is the nanopore event rate divided by concentration for a given molecule type. Specifically, the parameter $\alpha$ is the reference molecule capture rate constant divided by the target analyte capture rate constant. Thus, the multiplier $\alpha$ compensates for difference in nanopore capture and detection between the target and reference molecule types.

When the control mixture is a 1:1 ratio, $$\alpha = \left(\frac{Q_{targ} - Q_{X:Y}}{Q_{X:Y} - Q_{ref}}\right).$$

When compensation for a capture rate constant differential between a target analyte and a reference analyte is not used, $\alpha$ is set equal to 1 in equations (1) and (2), to provide the estimates for $F^*_{mix}$ and $R^*_{mix}$, respectively.

Applying equations (1) and (2) provide estimates for $F^*_{mix}$ and $R^*_{mix}$, respectively. Uncertainty estimates, or error bars, for $F^*_{mix}$ and $R^*_{mix}$ can also be computed. Each Q for the isolated and mixture controls and for the unknown mixture has a standard error associated with it, $std(Q) = \sqrt{Q(1-Q)/N}$, where N is the total number of events. Numerically, random samples from each Q distribution can be drawn many times, to generate a distribution of values for $F^*_{mix}$ and $R^*_{mix}$, by applying equations (1) and (2). Then distributions for $F^*_{mix}$ and $R^*_{mix}$ can then be used to compute uncertainty bounds, resulting in $F^*_{mix} \pm F^*_{sd}$ and $R^*_{mix} \pm R^*_{sd}$.

In some embodiments, the ratio or fraction of events matching or exceeding an event feature criterion is used to estimate the fractional amount of target to reference in an unknown mixture. In some embodiments, the criterion is a threshold.

Our previous work describes how a single tagging criterion is utilized to compute Q and its error bars (Morin, Trevor J, Tyler Shropshire, Xu Liu, Kyle Briggs, Cindy Huynh, Vincent Tabard-Cossa, Hongyun Wang, and William B Dunbar. "Nanopore-Based Target Sequence Detection." Edited by Meni Wanunu. PloS One 11, no. 5 (May 5, 2016): e0154426-21. doi: 10.1371/journal.pone.0154426). As detailed in that work, by applying the criterion, each event j has the variable $Z_j$ assigned to it. If event j is tagged, $Z_j=1$; otherwise, $Z_j=0$. For each reagent set (controls and unknowns), $Q=(\Sigma_j Z_j)/N$, where N is the total number of events. The same criterion is applied to all controls, isolated and mixtures, and all unknowns, to compute all Q values utilized in the formulas above (equations (1)-(2)).

The criterion involves one or more than one inequality equation, and can be a linear or nonlinear function of one or more event features. Each inequality equation has a threshold or range of thresholds associated with it. Thus, a criterion is fully specified by the set of inequalities and the corresponding set of thresholds.

In some embodiments, the criterion is established for a class of target and reference molecule types, and new assays using types of molecules for that class will utilize the criterion already established.

In some embodiments, the criterion is identified from the control data gathered for any new assay. That is, the criterion is established at run time as part of the fractional abundance protocol.

In some embodiments, the set of inequalities for the criterion are established a priori from sets of previous experiments using comparable target and reference molecule types, while the set of thresholds for the one or more criterion inequalities are established at run time using the control data.

In some embodiments, a single event feature is utilized in establishing the criterion.

A threshold, labeled "q," is the scalar value that divides target-tagged events from non-target-tagged (i.e., reference-tagged) events based on an inequality. When more than one inequality is used in a criterion, q can represent the vector of threshold values used for the set of inequalities.

Consider the example of using two different length dsDNA for the target and the reference. Commonly, a single inequality using the event area is a viable criterion. When the target is dsDNA that is longer than the reference dsDNA, events are tagged if the area exceeds a threshold. When the target is dsDNA that is shorter than the reference dsDNA, events are tagged if the area is less than a threshold.

Different methods can be utilized to automate selection of the q-threshold value or values, where one q value is identified with each inequality in the criterion.

In some embodiments, the q-threshold is found as the value that produces a desired false positive for $Q_{ref}$. For example, the q-threshold could be set at the $95^{th}$ percentile of $Q_{ref}$ to produce a false positive of 5%. In that case, 95% of the reference molecule events have an area less than q. Alternatively, the SFT q-threshold is found as the value that produces a desired false negative for $Q_{targ}$, i.e., the q-threshold could set at the $5^{th}$ percentile of $Q_{targ}$ to produce a false negative of 5%.

In some embodiments, the SFT q-threshold is found as the solution to $$\min_q \{Q_{targ}(q) - Q_{ref}(q)\}.$$

The threshold would the value that is corresponds to the greatest distance between $Q_{targ}$ end $Q_{ref}$.

In some embodiments, the q-threshold range is computed as the values that produce a desired false positive range for $Q_{ref}$. For example, the q-threshold ranges could span the $95^{th}$ to the $99^{th}$ percentiles of $Q_{ref}$.

In some embodiments, where a q-threshold range is utilized, equations (1) and (2) produce a ranges of $F^*_{mix}(q)$ and $R^*_{mix}(q)$ values, and the average of these ranges are computed and reported as the predicted $F^*_{mix}$ and $R^*_{mix}$ values.

Consider the example of using two different payloads bound to the target DNA and the reference DNA. Commonly, three inequalities using the event mean conductance and event duration are a viable criterion. Specifically, for specific payload-target DNA molecule constructs, the target events create a unique subspace on a 2D event plot of mean $\delta G$ vs. duration, and events are tagged when duration is greater than a threshold, and when mean $\delta G$ is above one threshold and below another threshold. In this case, the tagging criterion is represented by three linear inequalities and three thresholds, using two event features (mean $\delta G$, duration).

The SVM Method

In some embodiments, machine learning is used to identify the set of features and feature criterion for tagging each event as a target analyte event or a reference analyte event. In some embodiments, support vector machines are used to classify events as target or reference analytes.

In some embodiments, developing a support vector machine workflow has the follows the steps: 1) load nanopore data, 2) select nanopore event features to differentiate events, 3) model training and testing using controls, 4) data calibration using controls, 5) prediction of unknown target: reference mixtures. In some embodiments, an already developed and reduced support vector machine workflow is implemented for automated fractional abundance predictions.

In some embodiments, machine learning tools are applied to automate the selection of the criterion, including selection of the event features, the form of the inequalities (linear and/or nonlinear) and the threshold values q used in the inequalities. In some embodiments, Support Vector Machines (SVMs), a supervised machine learning method that solves classification problems, are implemented to generate the tagging criterion. References on SVMs include: Cortes, C. & Vapnik, V. Machine Learning (1995) 20: 273; and Boser, B. E., Guyon, I. M., and Vapnik, V. N. (1992). "A training algorithm for optimal margin classifiers," *Proceedings of the fifth annual workshop on Computational learning theory*, each of which is incorporated by reference in its entirety.

An example of an application of the SVM method to our fractional abundance framework is provided below:

For data that is linearly separable, let $\{x_1, \ldots, x_n\}$ be the data set and let $y_i \in \{1, -1\}$ be the class label of $x_i$, the decision boundary should classify all points by:

$$y_i(w^T x_i + b) \geq 1, \forall i$$

To maximize the margin classifying all points, the classification problem becomes the following optimization problem:

$$\text{Minimize } \tfrac{1}{2}\|w\|^2 \quad \text{(Equation 3)}$$

subject to $y_i(w^T x_i + b) \geq 1, \forall i$

The data points that are close to decision boundary are called support vectors.

Figure 3A:
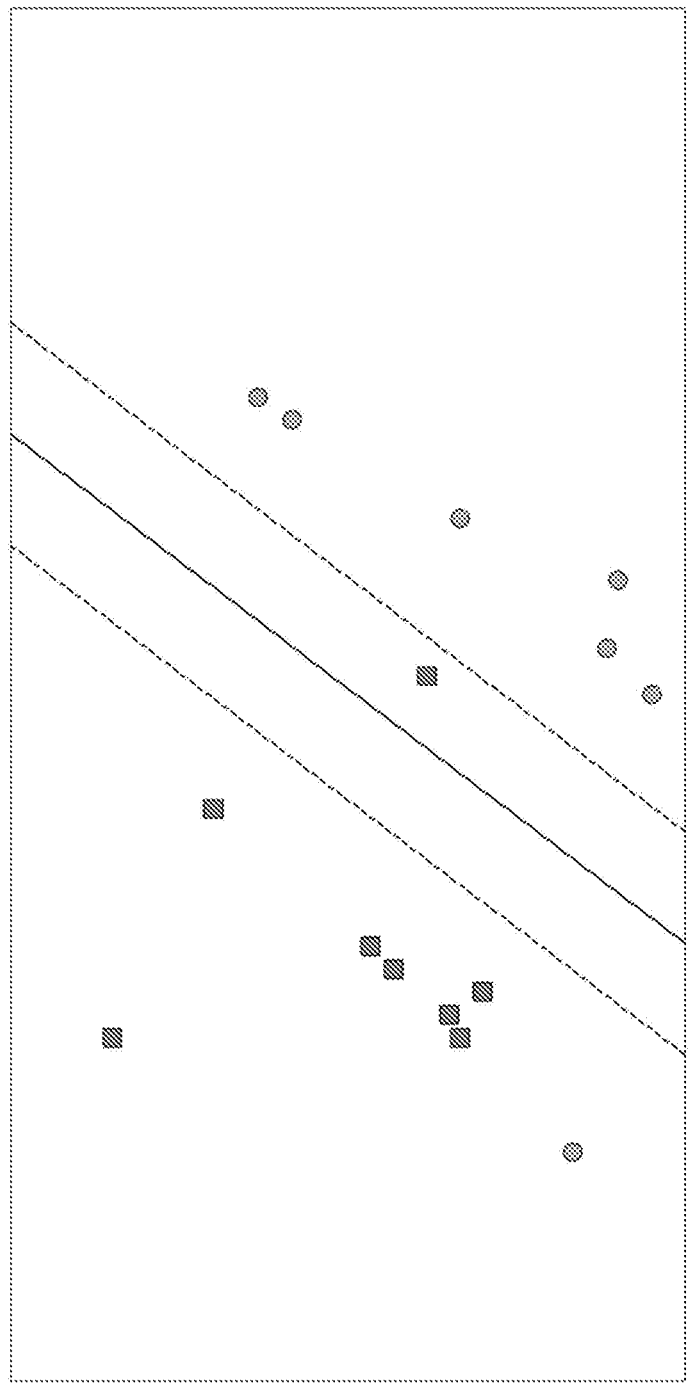
FIG. 3A depicts an example of a threshold generated between events from type 1 analytes (squares) and type 2 analytes (circles).

For real-word problems, data are usually not linearly separable because of some outliers or noises. To optimize the classification, the margin was adjusted to allow a few misclassified points. Meanwhile, the misclassified cases were punished with high costs. This margin becomes a soft margin. A soft margin classification can be used by adding "slack" variables into the cost function (FIG. 3A):

$$\text{Minimize } \tfrac{1}{2}\|w\|^2 + C\sum_{i=1}^{n} \varepsilon_i$$

subject to: $y_i(w^T x_i + b) \geq 1 - \varepsilon_i, \varepsilon_i \geq 0$

Figure 3B:
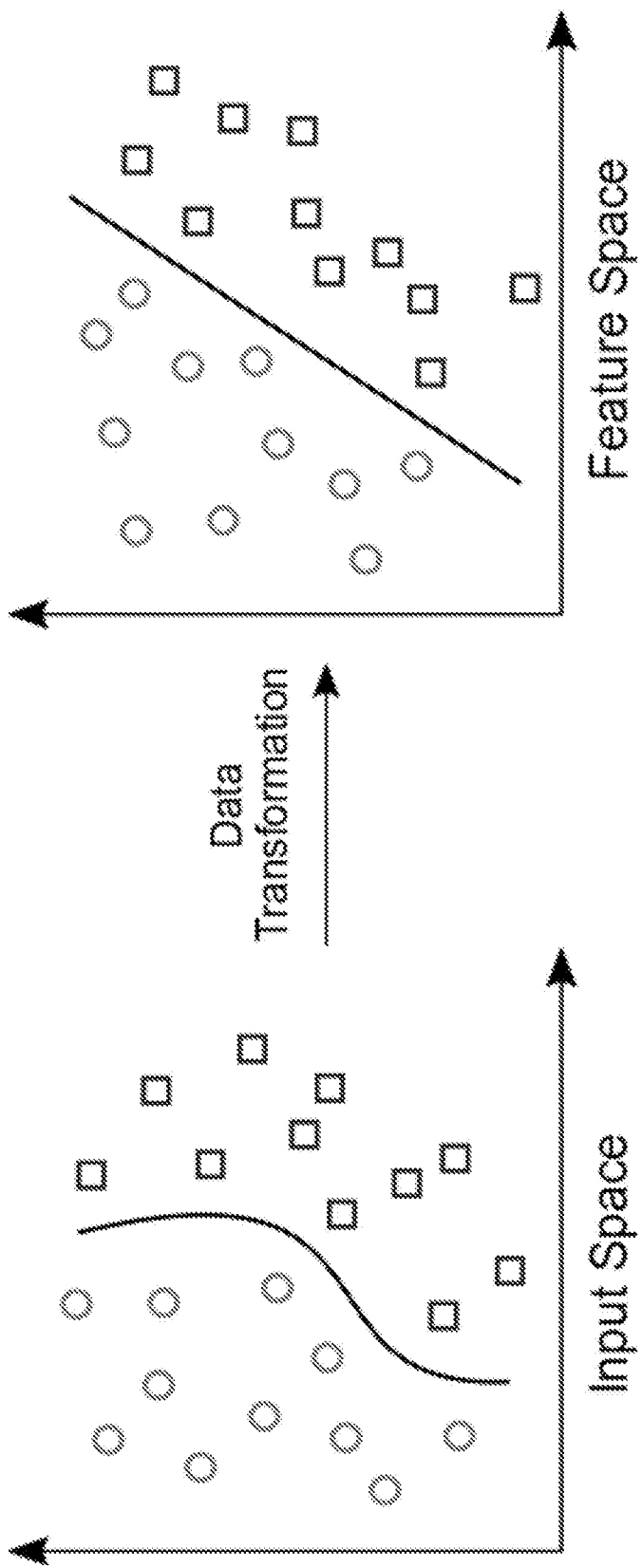
FIG. 3B shows an example of the results of transformation of input features to a higher dimensional space to increase the accuracy of a linear threshold between events from type 1 analytes (squares) and type 2 analytes (circles).

A second way to deal with linearly non-separable data is the kernel method (Boser, B. E., et al., cited above). It transforms the input feature space to a higher dimension space. By doing so, the data can be linearly separable (FIG. 3B). Denote the mapping function as $\emptyset(x)$, then the kernel function K can be written as:

$$K(x_i, x_j) = \emptyset(x_i)^T \emptyset(x_j) \quad \text{(Equation 4)}$$

There are sets of kernel function types available. The most common types are listed here:

Linear Kernel $$K(x_i, x_j) = x_i^T x_j + c$$

Polynomial Kernel $$K(x_i, x_j) = (\alpha x_i^T x_j + c)^d$$

Gaussian (RBF) Kernel $$K(x_i, x_j) = \exp(-\gamma \|x_i - x_j\|)$$

Usually, both Kernel tricks and soft margin are used together to produce a better solution for classification problems.

Applying SVM to nanopore data for fractional abundance has the following steps: 1) load control and unknown data sets, including all events for each set; 2) feature selection; 3) model training and testing; 4) data calibration; and 5) prediction of $F^*_{mix}$ and $R^*_{mix}$. In the examples provided, application of these 5 steps is demonstrated in greater detail. Equations (3) and (4), hyper-parameters grid search including Kernel types, soft margin constant, and any parameters that kernel function may depend on, are solved as part of applying the method. An assay based generalize model generated form SVM including common decision boundaries and common calibration ratio can be applied to unknown mixtures without requirement of control data sets.

An assay based generalized model generated from SVM including common decision boundaries and common calibration ratio can be applied to unknown mixtures without requirement of control data sets. Other data mining methods including decision tress, neural networks, Native Bayer, Logistic regress, K-nearest neighbor and boosting are also claimed as applicable methods for nanopore data.

The EMGM Method (Expectation Maximization Algorithm for Gaussian Mixtures)

In some embodiments, clustering methods are applied to create the criteria for tagging target events and reference events. Each event is tagged as a target event or a reference event. In some embodiments, the fractional abundance is the proportion of the target events relative to the sum of the target and reference events. Running controls that provide compensatory information allows adjustments that improve the estimate of the fractional abundance.

In some embodiments, the clustering method is a maximum likelihood method applied to parameterized models of the distributions of one or more event parameters. Iterative application of maximum likelihood estimation to control sets results in fitted model parameters, with one set of distributions associated with target analyte type and the other set of distributions associated with the reference analyte type. Subsequently, application of the parameterized models to unknown mixtures results in the assignment of events to either the target of the reference distribution(s), and the ratio of events assigned to the target distribution(s) to the total number of events assigned to target plus reference distribution(s) is used to generate the fractional amount estimate.

A log likelihood function is used as the metric for tracking progress in iterations of the algorithm, which recursively updates the membership assignment of each event in control data and improves the fit of the distributions to the data. In some embodiments, the data are modeled using mixtures of parameterized Gaussian distributions. Methods that use finite mixture models, including Gaussian mixture models, to characterize numerical data are well characterized in statistics and applied mathematics (Hand, David J., Heikki Mannila, and Padhraic Smyth. Principles of data mining. MIT press, 2001).

In some embodiments, given a Gaussian Mixture (GM) model, the method maximizes the likelihood function with respect to the parameters comprising the means and covariance of the components and the mixing coefficients. Since there is no closed-form solution for the log likelihood, the mode parameters and weights for assigning data to modes are iteratively computed using the Expectation Maximization (EM) technique (C. M. Bishop, Pattern Recognition and Machine Learning, Springer, 2006).

The method of applying an EM algorithm applied to GM models to nanopore data for the purpose of generating fraction abundance estimates is termed EMGM. Like the Q-test method, the EMGM method uses prior knowledge about one or more nanopore event signatures that can be used to distinguish the target events from the reference events.

As stated, the target population may be represented by a single distribution, or more than one distribution. Likewise, the reference population may be represented by a single distribution, or more than one distribution. The target and reference distribution(s) are established by applying the algorithm to one or more isolated controls and one or more control mixtures.

Subsequently, after the target distribution(s) are established, an event in an unknown mixture is tagged as a target event if it is associated with the modeled target distribution(s).

By example, a total of three Gaussian distributions could fit the entire data set in a 1:1 control mixture, with one mode associated with the target type and two modes associated with the reference type.

The algorithm requires only one control mixture for application of the EMGM. Subsequently, the resulting model can be applied to unknown mixtures. In some embodiments, an additional isolated reference control is used to offset the effects of false positives. Specifically, application of the EMGM models to 100% reference control established the false positive fraction, which is subtracted from the predicted fraction generated by applying the EMGM models to the unknown mixture. This subtraction can be referred to as false positive compensation (or "FP" compensation).

Nanopore Devices

A nanopore device, as provided, includes at least a pore that forms an opening in a structure separating an interior space of the device into two volumes, and at least a sensor configured to identify objects (for example, by detecting changes in parameters indicative of objects) passing through the pore. Nanopore devices used for the methods described herein are also disclosed in PCT Publication WO/2013/012881, incorporated by reference in its entirety.

The pore(s) in the nanopore device are of a nano scale or micro scale. In one aspect, each pore has a size that allows a small or large molecule or microorganism to pass. In one aspect, each pore is at least about 1 nm in diameter. Alternatively, each pore is at least about 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 25 nm, 30 nm, 35 nm, 40 nm, 45 nm, 50 nm, 60 nm, 70 nm, 80 nm, 90 nm, or 100 nm in diameter.

In one aspect, the pore is no more than about 100 nm in diameter. Alternatively, the pore is no more than about 95 nm, 90 nm, 85 nm, 80 nm, 75 nm, 70 nm, 65 nm, 60 nm, 55 nm, 50 nm, 45 nm, 40 nm, 35 nm, 30 nm, 25 nm, 20 nm, 15 nm, or 10 nm in diameter.

In one aspect, the pore has a diameter that is between about 1 nm and about 100 nm, or alternatively between about 2 nm and about 80 nm, or between about 3 nm and about 70 nm, or between about 4 nm and about 60 nm, or between about 5 nm and about 50 nm, or between about 10 nm and about 40 nm, or between about 15 nm and about 30 nm.

In some aspects, the nanopore device further includes means to move a polymer scaffold across the pore and/or means to identify objects that pass through the pore. Further details are provided below, described in the context of a two-pore device.

Compared to a single-pore nanopore device, a two-pore device can be more easily configured to provide good control of speed and direction of the movement of the polymer scaffold across the pores.

In one embodiment, the nanopore device includes a plurality of chambers, each chamber in communication with an adjacent chamber through at least one pore. Among these pores, two pores, namely a first pore and a second pore, are placed so as to allow at least a portion of a target polynucleotide to move out of the first pore and into the second pore. Further, the device includes a sensor at each pore capable of identifying the target polynucleotide during the movement. In one aspect, the identification entails identifying individual components of the target polynucleotide. In another aspect, the identification entails identifying payload molecules bound to the target polynucleotide. When a single sensor is employed, the single sensor may include two electrodes placed at both ends of a pore to measure an ionic current across the pore. In another embodiment, the single sensor comprises a component other than electrodes.

In one aspect, the device includes three chambers connected through two pores. Devices with more than three chambers can be readily designed to include one or more additional chambers on either side of a three-chamber device, or between any two of the three chambers. Likewise, more than two pores can be included in the device to connect the chambers.

In one aspect, there can be two or more pores between two adjacent chambers, to allow multiple polymer scaffolds to move from one chamber to the next simultaneously. Such a multi-pore design can enhance throughput of target polynucleotide analysis in the device. For multiplexing, one chamber could have a one type of target polynucleotide, and another chamber could have another target polynucleotide type.

In some aspects, the device further includes means to move a target polynucleotide from one chamber to another. In one aspect, the movement results in loading the target polynucleotide (e.g., the amplification product or amplicon comprising the target sequence) across both the first pore and the second pore at the same time. In another aspect, the means further enables the movement of the target polynucleotide, through both pores, in the same direction.

For instance, in a three-chamber two-pore device (a "two-pore" device), each of the chambers can contain an electrode for connecting to a power supply so that a separate voltage can be applied across each of the pores between the chambers.

In accordance with one embodiment of the present disclosure, provided is a device comprising an upper chamber, a middle chamber and a lower chamber, wherein the upper chamber is in communication with the middle chamber through a first pore, and the middle chamber is in communication with the lower chamber through a second pore. Such a device may have any of the dimensions or other characteristics previously disclosed in U.S. Publ. No. 2013-0233709, entitled Dual-Pore Device, which is herein incorporated by reference in its entirety.

In one aspect, each pore is at least about 1 nm in diameter. Alternatively, each pore is at least about 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 25 nm, 30 nm, 35 nm, 40 nm, 45 nm, 50 nm, 60 nm, 70 nm, 80 nm, 90 nm, or 100 nm in diameter.

In one aspect, each pore is no more than about 100 nm in diameter. Alternatively, the pore is no more than about 95 nm, 90 nm, 85 nm, 80 nm, 75 nm, 70 nm, 65 nm, 60 nm, 55 nm, 50 nm, 45 nm, 40 nm, 35 nm, 30 nm, 25 nm, 20 nm, 15 nm, or 10 nm in diameter.

In one aspect, the pore has a diameter that is between about 1 nm and about 100 nm, or alternatively between about 2 nm and about 80 nm, or between about 3 nm and about 70 nm, or between about 4 nm and about 60 nm, or between about 5 nm and about 50 nm, or between about 10 nm and about 40 nm, or between about 15 nm and about 30 nm.

In some aspects, the pore has a substantially round shape. "Substantially round", as used here, refers to a shape that is at least about 80 or 90% in the form of a cylinder. In some embodiments, the pore is square, rectangular, triangular, oval, or hexangular in shape.

In one aspect, the pore has a depth that is between about 1 nm and about 10,000 nm, or alternatively, between about 2 nm and about 9,000 nm, or between about 3 nm and about 8,000 nm, etc.

In some aspects, the nanopore extends through a membrane. For example, the pore may be a protein channel inserted in a lipid bilayer membrane or it may be engineered by drilling, etching, or otherwise forming the pore through a solid-state substrate such as silicon dioxide, silicon nitride, grapheme, or layers formed of combinations of these or other materials. Nanopores are sized to permit passage through the pore of the scaffold:fusion:payload, or the product of this molecule following enzyme activity. In other embodiments, temporary blockage of the pore may be desirable for discrimination of molecule types.

In some aspects, the length or depth of the nanopore is sufficiently large so as to form a channel connecting two otherwise separate volumes. In some such aspects, the depth of each pore is greater than 100 nm, 200 nm, 300 nm, 400 nm, 500 nm, 600 nm, 700 nm, 800 nm, or 900 nm. In some aspects, the depth of each pore is no more than 2000 nm or 1000 nm.

In one aspect, the pores are spaced apart at a distance that is between about 10 nm and about 1000 nm. In some aspects, the distance between the pores is greater than 1000 nm, 2000 nm, 3000 nm, 4000 nm, 5000 nm, 6000 nm, 7000 nm, 8000 nm, or 9000 nm. In some aspects, the pores are spaced no more than 30000 nm, 20000 nm, or 10000 nm apart. In one aspect, the distance is at least about 10 nm, or alternatively, at least about 20 nm, 30 nm, 40 nm, 50 nm, 60 nm, 70 nm, 80 nm, 90 nm, 100 nm, 150 nm, 200 nm, 250 nm, or 300 nm. In another aspect, the distance is no more than about 1000 nm, 900 nm, 800 nm, 700 nm, 600 nm, 500 nm, 400 nm, 300 nm, 250 nm, 200 nm, 150 nm, or 100 nm.

In yet another aspect, the distance between the pores is between about 20 nm and about 800 nm, between about 30 nm and about 700 nm, between about 40 nm and about 500 nm, or between about 50 nm and about 300 nm.

The two pores can be arranged in any position so long as they allow fluid communication between the chambers and have the prescribed size and distance between them. In one aspect, the pores are placed so that there is no direct blockage between them. Still, in one aspect, the pores are substantially coaxial.

In one aspect, the device has electrodes in the chambers connected to one or more power supplies. In some aspects, the power supply includes a voltage-clamp or a patch-clamp, which can supply a voltage across each pore and measure the current through each pore independently. In this respect, the power supply and the electrode configuration can set the middle chamber to a common ground for both power supplies. In one aspect, the power supply or supplies are configured to apply a first voltage $V_1$ between the upper chamber (Chamber A) and the middle chamber (Chamber B), and a second voltage $V_2$ between the middle chamber and the lower chamber (Chamber C).

In some aspects, the first voltage $V_1$ and the second voltage $V_2$ are independently adjustable. In one aspect, the middle chamber is adjusted to be a ground relative to the two voltages. In one aspect, the middle chamber comprises a medium for providing conductance between each of the pores and the electrode in the middle chamber. In one aspect, the middle chamber includes a medium for providing a resistance between each of the pores and the electrode in the middle chamber. Keeping such a resistance sufficiently small relative to the nanopore resistances is useful for decoupling the two voltages and currents across the pores, which is helpful for the independent adjustment of the voltages.

Adjustment of the voltages can be used to control the movement of charged particles in the chambers. For instance, when both voltages are set in the same polarity, a properly charged particle can be moved from the upper chamber to the middle chamber and to the lower chamber, or the other way around, sequentially. In some aspects, when the two voltages are set to opposite polarity, a charged particle can be moved from either the upper or the lower chamber to the middle chamber and kept there.

The adjustment of the voltages in the device can be particularly useful for controlling the movement of a large molecule, such as a charged polymer scaffold, that is long enough to cross both pores at the same time. In such an aspect, the direction and the speed of the movement of the molecule can be controlled by the relative magnitude and polarity of the voltages as described below.

The device can contain materials suitable for holding liquid samples, in particular, biological samples, and/or materials suitable for nanofabrication. In one aspect, such materials include dielectric materials such as, but not limited to, silicon, silicon nitride, silicon dioxide, graphene, carbon nanotubes, $TiO_2$, $HfO_2$, $Al_2O_3$, or other metallic layers, or any combination of these materials. In some aspects, for example, a single sheet of graphene membrane of about 0.3 nm thick can be used as the pore-bearing membrane.

Devices that are microfluidic and that house two-pore microfluidic chip implementations can be made by a variety of means and methods. For a microfluidic chip comprised of two parallel membranes, both membranes can be simultaneously drilled by a single beam to form two concentric pores, though using different beams on each side of the membranes is also possible in concert with any suitable alignment technique. In general terms, the housing ensures sealed separation of Chambers A-C.

In one aspect, the device includes a microfluidic chip (labeled as "Dual-pore chip") is comprised of two parallel membranes connected by spacers. Each membrane contains a pore drilled by a single beam through the center of the membrane. Further, the device preferably has a Teflon® housing or polycarbonate housing for the chip. The housing ensures sealed separation of Chambers A-C and provides minimal access resistance for the electrode to ensure that each voltage is applied principally across each pore.

More specifically, the pore-bearing membranes can be made with transmission electron microscopy (TEM) grids with a 5-100 nm thick silicon, silicon nitride, or silicon dioxide windows. Spacers can be used to separate the membranes, using an insulator, such as SU-8, photoresist, PECVD oxide, ALD oxide, ALD alumina, or an evaporated metal material, such as Ag, Au, or Pt, and occupying a small volume within the otherwise aqueous portion of Chamber B between the membranes. A holder is seated in an aqueous bath that is comprised of the largest volumetric fraction of Chamber B. Chambers A and C are accessible by larger diameter channels (for low access resistance) that lead to the membrane seals.

A focused electron or ion beam can be used to drill pores through the membranes, naturally aligning them. The pores can also be sculpted (shrunk) to smaller sizes by applying a correct beam focusing to each layer. Any single nanopore drilling method can also be used to drill the pair of pores in the two membranes, with consideration to the drill depth possible for a given method and the thickness of the membranes. Predrilling a micro-pore to a prescribed depth and then a nanopore through the remainder of the membranes is also possible to further refine the membrane thickness.

By virtue of the voltages present at the pores of the device, charged molecules can be moved through the pores between chambers. Speed and direction of the movement can be controlled by the magnitude and polarity of the voltages. Further, because each of the two voltages can be independently adjusted, the direction and speed of the movement of a charged molecule can be finely controlled in each chamber.

One example concerns a target polynucleotide, having a length that is longer than the combined distance that includes the depth of both pores plus the distance between the two pores. For example, a 1000 by dsDNA is about 340 nm in length, and would be substantially longer than the 40 nm spanned by two 10 nm-deep pores separated by 20 nm. In a first step, the polynucleotide is loaded into either the upper or the lower chamber. By virtue of its negative charge under a physiological condition at a pH of about 7.4, the polynucleotide can be moved across a pore on which a voltage is applied. Therefore, in a second step, two voltages, in the same polarity and at the same or similar magnitudes, are applied to the pores to move the polynucleotide across both pores sequentially.

At about the time when the polynucleotide reaches the second pore, one or both of the voltages can be changed. Since the distance between the two pores is selected to be shorter than the length of the polynucleotide, when the polynucleotide reaches the second pore, it is also in the first pore. A prompt change of polarity of the voltage at the first pore, therefore, will generate a force that pulls the polynucleotide away from the second pore.

Assuming that the two pores have identical voltage-force influence and $|V_1|=|V_2|+\delta V$, the value $\delta V > 0$ (or $<0$) can be adjusted for tunable motion in the $|V_1|$ (or $V_2$) direction. In practice, although the voltage-induced force at each pore will not be identical with $V_1=V_2$, calibration experiments can identify the appropriate bias voltage that will result in equal pulling forces for a given two-pore chip; and variations around that bias voltage can then be used for directional control.

If, at this point, the magnitude of the voltage-induced force at the first pore is less than that of the voltage-induced force at the second pore, then the polynucleotide will continue crossing both pores towards the second pore, but at a lower speed. In this respect, it is readily appreciated that the speed and direction of the movement of the polynucleotide can be controlled by the polarities and magnitudes of both voltages. As will be further described below, such a fine control of movement has broad applications. For quantitating target polynucleotides, the utility of two-pore device implementations is that during controlled delivery and sensing, the target polynucleotide or payload-bound target polynucleotide can be repeatedly measured, to add confidence to the detection result.

Accordingly, in one aspect, provided is a method for controlling the movement of a charged polymer scaffold through a nanopore device. The method comprises (a) loading a sample comprising a target polynucleotide (e.g., a target polynucleotide amplicon) in one of the upper chamber, middle chamber or lower chamber of the device of any of the above embodiments, wherein the device is connected to one or more power supplies for providing a first voltage between the upper chamber and the middle chamber, and a second voltage between the middle chamber and the lower chamber; (b) setting an initial first voltage and an initial second voltage so that the target polynucleotide moves between the chambers, thereby locating the polymer scaffold across both the first and second pores; and (c) adjusting the first voltage and the second voltage so that both voltages generate force to pull the charged target polynucleotide away from the middle chamber (voltage-competition mode), wherein the two voltages are different in magnitude, under controlled conditions, so that the target polynucleotide scaffold moves across both pores in either direction and in a controlled manner.

In one aspect, the sample containing the target polynucleotide is loaded into the upper chamber and the initial first voltage is set to pull the target polynucleotide from the upper chamber to the middle chamber and the initial second voltage is set to pull the target polynucleotide from the middle chamber to the lower chamber. Likewise, the sample can be initially loaded into the lower chamber, and the target polynucleotide can be pulled to the middle and the upper chambers.

In another aspect, the sample containing the target polynucleotide is loaded into the middle chamber; the initial first voltage is set to pull the charged polymer scaffold from the middle chamber to the upper chamber; and the initial second voltage is set to pull the target polynucleotide from the middle chamber to the lower chamber.

In one aspect, real-time or on-line adjustments to the first voltage and the second voltage at step (c) are performed by active control or feedback control using dedicated hardware and software, at clock rates up to hundreds of megahertz. Automated control of the first or second or both voltages is based on feedback of the first or second or both ionic current measurements.

Sensors

As discussed above, in various aspects, the nanopore device further includes one or more sensors to carry out the detection of the target polynucleotide.

The sensors used in the device can be any sensor suitable for identifying a target polynucleotide amplicon bound or unbound to a payload molecule. For instance, a sensor can be configured to identify the target polynucleotide by measuring a current, a voltage, a pH value, an optical feature, or residence time associated with the polymer. In other aspects, the sensor may be configured to identify one or more individual components of the target polynucleotide or one or more components bound or attached to the target polynucleotide. The sensor may be formed of any component configured to detect a change in a measurable parameter where the change is indicative of the target polynucleotide, a component of the target polynucleotide, or preferably, a component bound or attached to the target polynucleotide. In one aspect, the sensor includes a pair of electrodes placed at two sides of a pore to measure an ionic current across the pore when a molecule or other entity, in particular a target polynucleotide, moves through the pore. In certain aspects, the ionic current across the pore changes measurably when a target polynucleotide segment passing through the pore is bound to a payload molecule. Such changes in current may vary in predictable, measurable ways corresponding with, for example, the presence, absence, and/or size of the target polynucleotide molecule present.

In a preferred embodiment, the sensor comprises electrodes that apply voltage and are used to measure current across the nanopore. Translocations of molecules through the nanopore provides electrical impedance (Z) which affects current through the nanopore according to Ohm's Law, $V=IZ$, where V is voltage applied, I is current through the nanopore, and Z is impedance. Inversely, the conductance $G=1/Z$ are monitored to signal and quantitate nanopore events. The result when a molecule translocates through a nanopore in an electrical field (e.g., under an applied voltage) is a current signature that may be correlated to the molecule passing through the nanopore upon further analysis of the current signal.

When residence time measurements from the current signature are used, the size of the component can be correlated to the specific component based on the length of time it takes to pass through the sensing device.

In one embodiment, a sensor is provided in the nanopore device that measures an optical feature of the polymer, a component (or unit) of the polymer, or a component bound or attached to the polymer. One example of such measurement includes the identification of an absorption band unique to a particular unit by infrared (or ultraviolet) spectroscopy.

In some embodiments, the sensor is an electric sensor. In some embodiments, the sensor detects a fluorescent signature. A radiation source at the outlet of the pore can be used to detect that signature.

Equivalents and Scope

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, Proteins: Structures and Molecular Properties (W. H. Freeman and Company, 1993); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.); Remington's Pharmaceutical Sciences, 18th Edition (Easton, Pa.: Mack Publishing Company, 1990); Carey and Sundberg Advanced Organic Chemistry 3rd Ed. (Plenum Press) Vols A and B(1992).

Example 1—Q-Test Based FA Using Different Length dsDNA for Target and Reference

This example presents results from the application of the fractional abundance (FA) framework to data in which a transgenic (GMO) target sequence is within a 788 bp target dsDNA (i.e., a target analyte) and the reference sequence (lectin housekeeping gene) is within a 466 bp reference dsDNA (i.e., a reference analyte). Quantitation of the fractional amount of transgene target in a sample is achieved below, first by applying the Q-test method with a single feature criterion based on event area and using equations (1) and (2), and second by applying the SVM method and using equations (3) and (4).

The 466 bp reference DNA and 788 bp target transgenic DNA fragments were generated by PCR from mixtures of conventional and transgene-containing genomic DNA samples using sequence specific oligonucleotide primers. PCR products were purified and concentrated using standard silica membrane columns. Precise fractional mixtures of the two amplicons were prepared from large volumes of the individually generated amplicons, and aliquots of the fractional mixtures and single amplicons were used as standard reference materials for all assays.

First, the reference control sample containing the 466 bp reference DNA was measured in a nanopore device. Next, the target control sample containing the 788 bp transgenic DNA was prepared and measured in the nanopore device. The length differences between the target analyte (788 bp) and the reference analyte (466 bp) generate a unique event signature upon translocation through the nanopore that can be discriminated based on area of the event signature.

Figure 4A:
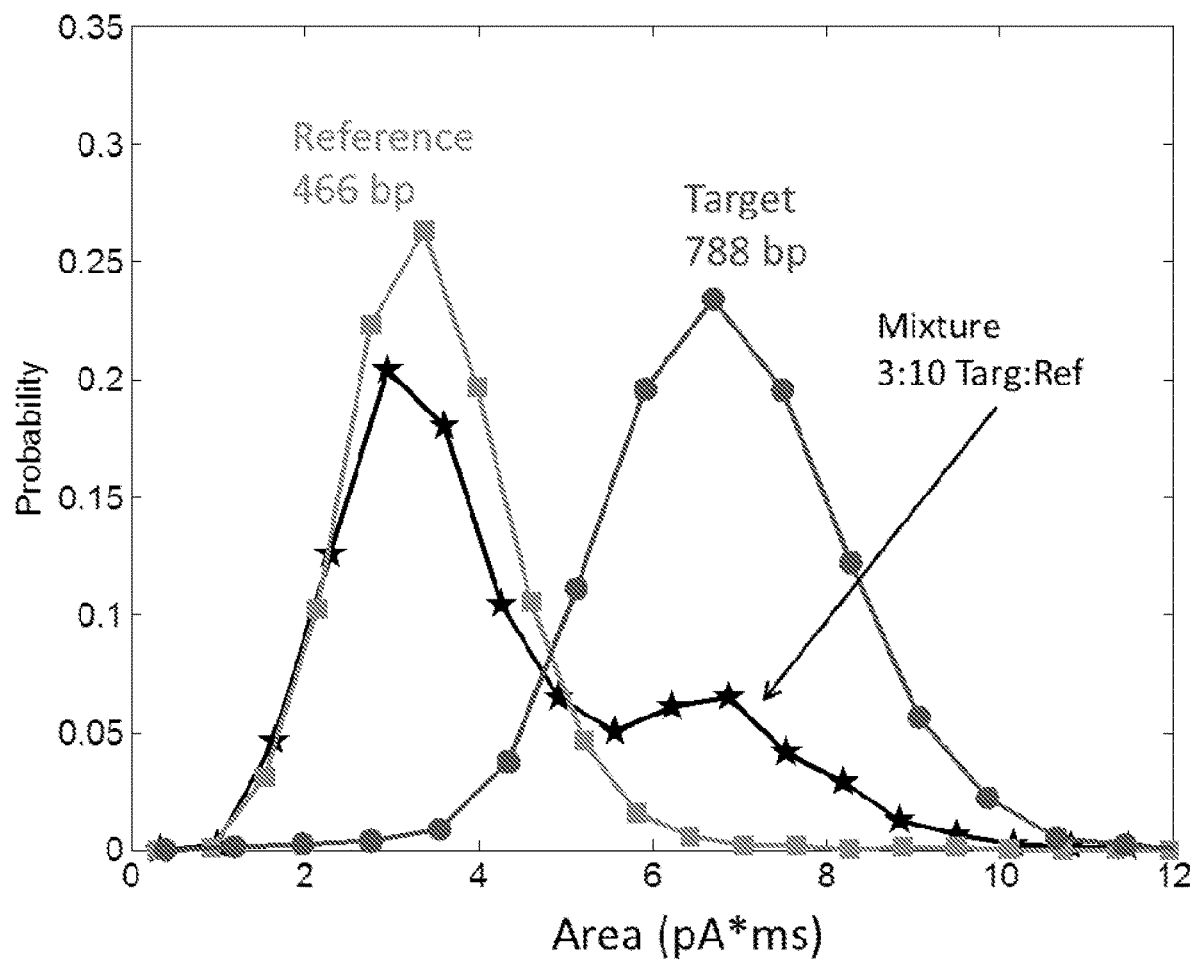
FIG. 4A shows a probability histogram for all events from a reference analyte sample, a target analyte sample, and a mixed sample according to event area.
Figure 4B:
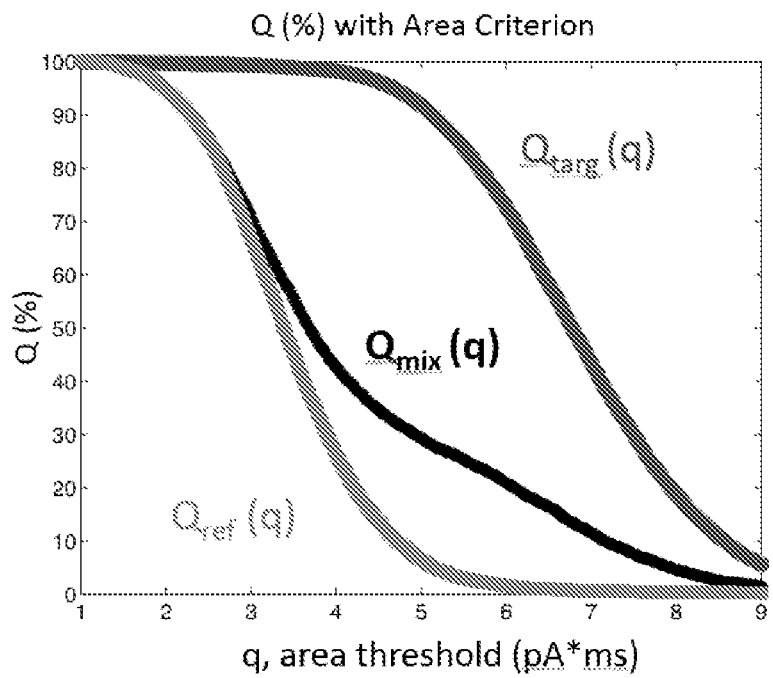
FIG. 4B depicts a graph of the percentage of events that are below an area threshold from reference analyte only (Qref), target analyte only (Qtarg), and a mixed sample of target analytes and reference analytes (Qmix).
Figure 4C:
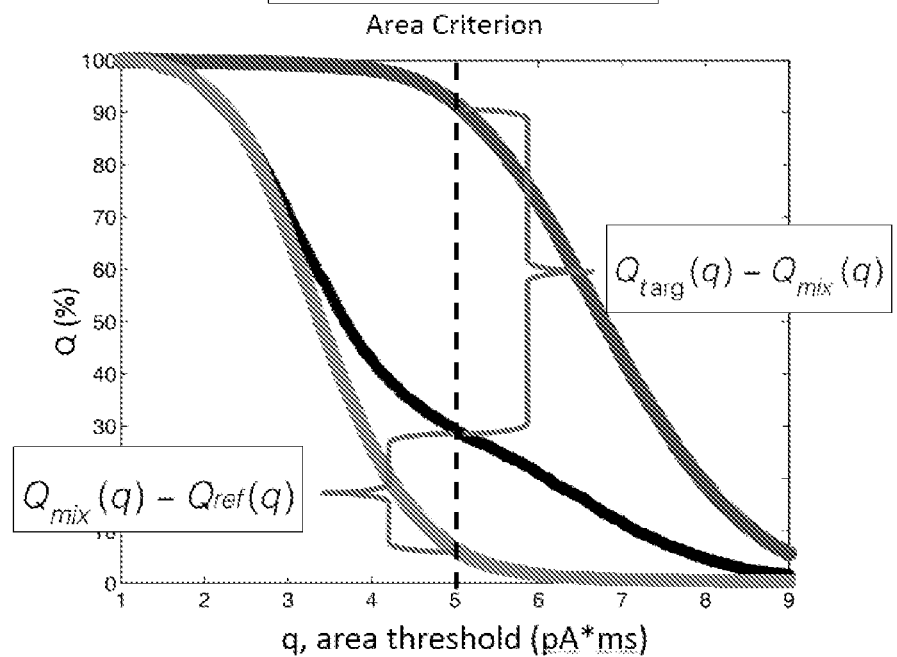
FIG. 4C shows how fractional amount parameter ρ(q) appears graphically at a q value. The q=5 pA*ms threshold (vertical dashed line) corresponds to a false positive of 0.05 (i.e., $Q_{ref}$=0.05) and a false negative of 0.1 (i.e., $Q_{targ}$=0.9).

FIG. 4A shows all event area histograms for two isolated control runs, one for the 466 bp reference DNA and one for the 788 bp target transgenic DNA. Also shown is an area histogram from a 3:10 target:reference control mixture. FIG. 4B shows the control mixtures ($Q_{targ}$, $Q_{ref}$) and the known mixture ($Q_{mix}$) trends as a function of the area criterion threshold q, where $Q_{mix}=Q_{3:10}$. FIG. 4C shows and how the fractional amount parameter $\rho(q)$ appears graphically at a q value. The q=5 pA*ms threshold (vertical dashed line) corresponds to a false positive of 0.05 (i.e., $Q_{ref}=0.05$) and a false negative of 0.1 (i.e., $Q_{targ}=0.9$).

Figure 5A:
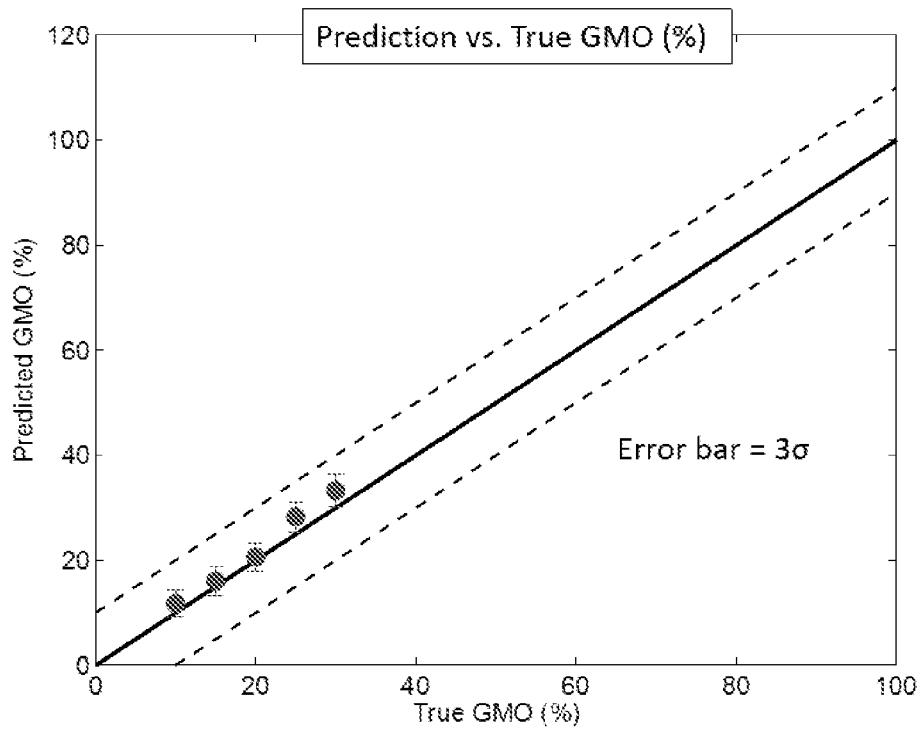
FIG. 5A shows the results of a determination of an estimate of a relative abundance of target gene (GMO (%)) ($R^*_{mix}$) vs. the true relative abundance of a target gene (GMO (%)). 10% error margins above and below the zero-error line (slope=1) are shown for comparison.

Application of equation (2) to generate $R^*_{mix}$ as the predicted GMO (%) is done here using the control mixtures, to test the accuracy and precision of the method of using reference only and target only controls to generate an estimate of fractional abundance for the known mixture. Equation (2) was first applied to known mixtures. Since no control mixture sample was used to generate, ($Q_{X:Y}$), the estimate was generated without using compensation for a capture rate constant differential between a target analyte and a reference analyte (i.e., setting $\alpha=1$) to validate the model. FIG. 5A shows a plot of the predicted GMO (%) ($R^*_{mix}$) vs. true GMO (%), and for comparison 10% error margins above and below the zero-error line (slope=1). These results were established by running 100% target and 100% reference (isolated) controls followed by five known mixtures, serially on a single nanopore. Table 1 reports the predicted values and error bars plotted in FIG. 5A, and the total number of events detected for each mixture.

TABLE 1

GMO prediction results for FIG. 5A data

| True GMO % | Predicted GMO % | Percent Error (Pred. - True) | Total events |
|---|---|---|---|
| 10% | 12.0 ± 1.07% | 2.0 ± 1.0% | 5,225 |
| 15% | 16.3 ± 1.1% | 1.3 ± 1.1% | 4,267 |
| 20% | 20.8 ± 1.1% | 0.75 ± 1.1% | 6,605 |
| 25% | 29.3 ± 1.2% | 4.3 ± 1.2% | 6,647 |
| 30% | 34.5 ± 1.4% | 4.4 ± 1.4% | 5,605 |

Figure 5B:
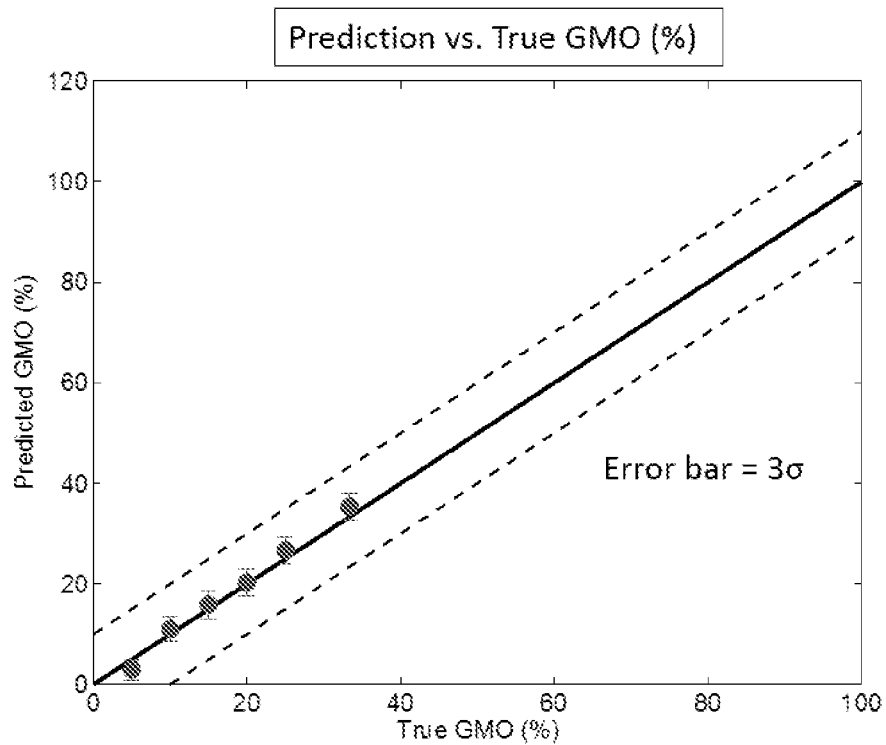
FIG. 5B shows the results of a determination of an estimate of the true relative abundance of genetically modified organisms in a sample using two isolated controls and six known mixtures. Values of predicted target abundance percentage were plotted against true target abundance percentage. 10% error margins above and below the zero-error line (slop=1) are shown for comparison.

A separate nanopore experiment following a similar protocol (two isolated controls, and six known mixtures) and produced the results shown in FIG. 5B and Table 2.

TABLE 2

GMO prediction results for FIG. 5B data

| True GMO % | Predicted GMO % | Percent Error (Pred. - True) | Total events |
|---|---|---|---|
| 5% | 2.87 ± 0.7% | -2.1 ± 0.7% | 4,783 |
| 10% | 11.1 ± 0.93% | 1.1 ± 0.9% | 4,884 |

TABLE 2-continued

GMO prediction results for FIG. 5B data

| True GMO % | Predicted GMO % | Percent Error (Pred. - True) | Total events |
|---|---|---|---|
| 15% | 16 ± 1.1% | 1.0 ± 1.1% | 4,326 |
| 20% | 20.4 ± 1.1% | 0.35 ± 1.1% | 5,895 |
| 25% | 27.1 ± 1.2% | 2.1 ± 1.2% | 6,587 |
| 33.33% | 36.2 ± 1.3% | 2.8 ± 1.3% | 7,862 |

The results from FIG. 5A and FIG. 5B and Tables 1 and 2 suggest that GMO % prediction accuracy within 5% is possible for discriminating two DNA lengths using a single nanopore. These results were achieved without using compensation for a capture rate constant differential between a target analyte and a reference analyte (setting $\alpha=1$ in equation (2)). Compensation for a capture rate constant differential is expected to further improve results.

Figure 6:
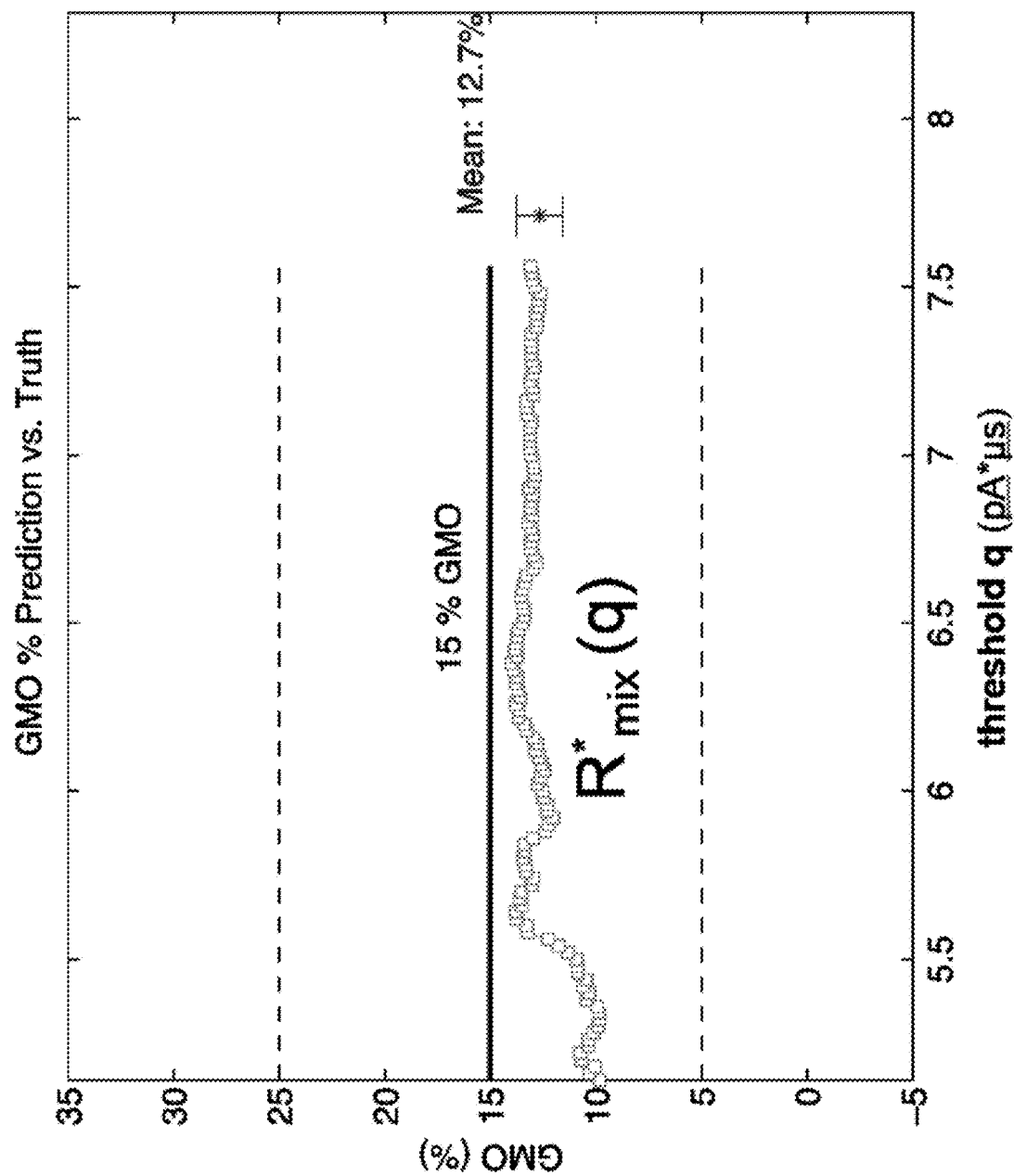
FIG. 6 shows the results of estimate of target analyte abundance (GMO (%)) over a range of thresholds for discriminating target analyte from reference analyte according to area of an event.

An example of when a q-threshold range is utilized, instead of a single value, is shown in FIG. 6. Specifically, the q-threshold range was chosen to span the $75^{th}$ to the $99^{th}$ percentiles of $Q_{ref}$. Plotted the resulting $R^*_{mix}(q)$ trend over the q range, and the average value mean$\{R^*_{mix}(q)\}=12.7\%$ compared to the known 15% GMO. This shows that the analysis framework provided herein can compensate for false positive and false negative errors over a range of thresholds, even when the threshold is not optimized, to provide an improved estimate of relative abundance of a target analyte in a sample.

The workflow demonstrated in this example for quantitating the abundance of a target sequence in a population did not require any amplification, purification, concentration or buffer exchange steps. This workflow is compatible with inexpensive, disposable sample prep cartridges, to allow a sample-in answer-out workflow in a miniaturized (handheld or desk top) unit.

In another set of experiments, varying GMO % samples were tested as unknowns. The protocol followed on each nanopore was: a) 100% 466 bp reference for 5 minutes, then flush; b) 100% 788 bp target for 5 minutes, then flush; c) run between 1 and 4 unknowns, each for 5 minutes, flushing in-between; d) run a control mixture. Area criterion was used and a q-threshold range spanning the $75^{th}$ to the $99^{th}$ percentiles of $Q_{ref}$ was implemented, reporting the average $R^*_{mix}(q)$ as the predicted GMO %. In equation (2), the control mixture was used for compensation for a capture rate constant differential between a target analyte and a reference analyte. Experiments used a target:reference control mixture of 1:1, 0.75:1 or 0.35:1.

Table 3 reports prediction results from one nanopore assay for four "unknown" mixed samples (S1-S4) using a control mixture of 0.35:1 (35% GMO) for compensation. Unknown were blinded in each nanopore assay, so the percent error is not reported in the table. The table also reports the total number of events recorded in each 5 minute period.

TABLE 3

GMO prediction results for blinded samples S1-S4

| True GMO % | Predicted GMO % | Total events |
|---|---|---|
| *35% | 35.1 ± 3.0% | 1,175 |
| Sample S1 | 32.0 ± 2.2% | 2,039 |
| Sample S2 | 10.2 ± 1.4% | 1,767 |

TABLE 3-continued

GMO prediction results for blinded samples S1-S4

| True GMO % | Predicted GMO % | Total events |
|---|---|---|
| Sample S3 | 20.9 ± 2.4% | 1,031 |
| Sample S4 | 6.2 ± 1.4% | 1,125 |

At total of 12 nanopore experiments were performed following the protocol stated above, and each mixed sample was tested 2-5 times, always on a different nanopore, and by a different experimenter or on a different date. Nanopore size range was 25-35 nm in diameter. A total of 11 mixed samples (S1-S11) were assayed. Table 4 reports the combined estimates, ordered from smallest to largest predicted GMO % value. The reported mean GMO % values are computed by averaging the single-nanopore predictions. The uncertainty of each mean estimate is computed from repeated random sampling of the individual estimates distributions (a Monte Carlo method). Reported is the numerically generated $95^{th}$-percentile confidence interval. The number of times each sample was tested and the true GMO % for each sample are also reported.

TABLE 4

Combined GMO % prediction (mean ± 2 sigma) for samples S1-S11

| Sample No. | No. Tests | Mean GMO % | True GMO % | Percent Error (Pred. - True) |
|---|---|---|---|---|
| S4 | 2 | 7.3 ± 2.9% | 5% | +2.3% |
| S2 | 2 | 10.2 ± 2.1% | 10% | +0.2% |
| S9 | 2 | 14.9 ± 2.4% | 15% | −0.1% |
| S3 | 2 | 21.2 ± 3.1% | 20% | +1.2% |
| S7 | 4 | 24.9 ± 2.3% | 25% | −0.1% |
| S1 | 2 | 33.8 ± 4.1% | 35% | −1.2% |
| S8 | 4 | 41.3 ± 2.9% | 42.5% | −1.2% |
| S5 | 4 | 67.0 ± 4.2% | 67.5% | −0.5% |
| S11 | 3 | 76.1 ± 6.8% | 75% | +1.1% |
| S10 | 5 | 88.9 ± 3.8% | 90% | −1.1% |
| S6 | 2 | 104 ± 7.1% | 100% | +4% |

The results from Table 4 show that our method can predict a fractional abundance of a target analyte (e.g., GMO %) with high accuracy. Within the range 10-90% GMO, accuracy is within 2% by combining single-nanopore estimates. Between 5-10% and at 100% GMO, where prediction errors could be expected to increase by approaching saturation limits, combining two nanopore estimates resulted in <5% error. In general, the use of compensation for a capture rate constant differential between a target analyte and a reference analyte improves accuracy compared to no compensation for the capture rate constant differential (Tables 1-2). For the entire GMO % prediction range, more nanopore estimates will greater improve accuracy and precision. Arrayed nanopores, each measuring from a common pool, can also reduce uncertainty further, by eliminating the person-to-person and day-to-day, and reagent set-to-set variations that were present as part of this study.

Example 2—SVM-Based FA Using Different Length dsDNA for Target and Reference

The same nanopore data recorded and analyzed in Example 1 was re-analyzed here using the SVM method presented previously (equations (3)-(4)).

The isolated control sets were first used for initial feature selection. The initial selection aims to remove highly correlated features, which can cause multicollinearity problems for certain classification methods. The seven identified features were: (i) $\log_{10}$(dwell), or just "dwell", the base-10 logarithm of event duration; (ii) maxAmp: the max δG; (iii) sdAmpSub: standard deviation of the event signal, removing rise and fall time; (iv) medAmp: the median δG; (v) LFNmean: mean of the noise power of the event below 50 Hz; (vi) LFNmedian: median of the noise power of the event below 50 Hz; (vii) Area: the same event area used in Example 1.

Further feature extraction was performed to reduce data dimensions. The purpose of this step is to balance computation time and classification accuracy. Two algorithms have been implemented: 1) Univariate feature selection method. The ANOVA F-value was computed between each feature and label of the event. A threshold was set manually to select a portion of features that have highest F scores. 2) Recursive feature elimination (RFE). The estimator (such as SVM) is trained on the initial set of features and the importance of each feature is obtained. Least important features will be excluded from current set of features. This procedure is recursively repeated until desired number of feature set is reached.

For the example 1 data, univariate feature selection method was employed. The threshold of percentage of features was manually set to 60%. The four optimal features chosen by algorithm were: (i) dwell, (ii) sdAmpSub, (iii), medAmp, (iv) Area.

Figure 7:
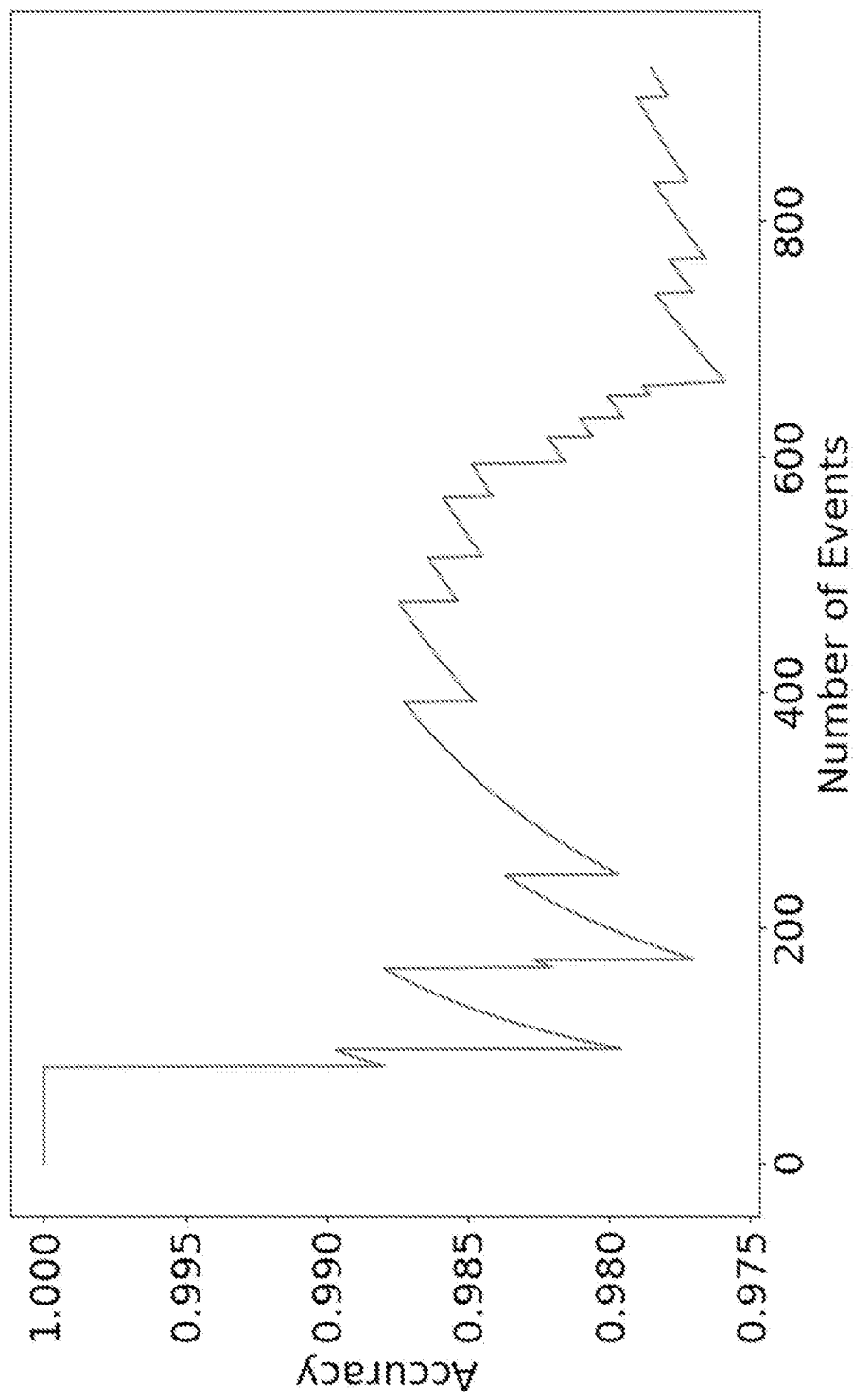
FIG. 7 shows a prediction of accuracy across a set of testing data from a trained support vector machine with optimal parameters for discriminating event signatures from target and reference analytes.

The next step in the method is model training and testing. All events collectively in the isolated controls were randomly sorted into a training dataset and a testing dataset using a 7:3 split. An SVM was trained based on the training dataset with hyper-parameters search algorithm to find the optimal parameters to perform classification. The hyper-parameters tested in grid algorithm are: the kernel type (linear, rbf), regularization parameter (C) and kernel coefficient (gamma). Area Under the Curve of ROC curve (roc_auc) was used to evaluate the performance of each hyper-parameters combination. The model having highest roc_auc scores was used for the down-stream data processing. For the best parameter combination, the average precision and recall of each class from the testing data were calculated. The model with optimal parameters was then trained by training dataset and tested on testing dataset. Prediction of accuracy on testing data set was generated and is shown in FIG. 7. The accuracy across the entire set remained above 97.5%.

The next step in the method was data calibration. Calibration can be achieved by applying the model in step 3 to the control mixture data, which generates a correction ratio. The correction ratio is then multiplied by each predicted amount for a unknown mixture. This is equivalent to multiplying by the parameter α in equations (1) and (2). The value for the parameter α is generated by the applying the model to the control mixture in the SVM method, whereas (1) and (2) involve direct calculation of a from the control data sets Q values.

Table 5 shows a comparison of GMO % predictions between the Q-test method and the SVM-based method.

TABLE 5

Comparing single nanopore GMO % predictions, Q-test vs. SVM

| Sample # | True GMO % | Q-test GMO % | SVM GMO % |
|---|---|---|---|
| 1. | 35% | 28.5% | 34.5% |
| 2. | 75% | 80.6% | 89.9% |
| 3. | 20% | 20.9% | 23.4% |
| 4. | 100% | 101.1% | 102% |
| 5. | 10% | 7.2% | 11.6% |
| 6. | 50% | 55.3% | 51.79% |
| 7. | 75% | 78.8% | 70.6% |
| 8. | 35% | 32.3% | 34.88% |
| 9. | 75% | 82.0% | 81.37% |
| 10. | 10% | 10.13% | 14% |
| 11. | 15% | 17.17% | 19.7% |
| 12. | 20% | 20.9% | 22.1% |
| 13. | 87.5% | 77.8% | 77.2% |
| 14. | 42.5% | 42.2% | 43.8% |
| 15. | 75% | 73.6% | 72% |
| 16. | 35% | 40.9% | 39.5% |
| 17. | 25% | 28.7% | 18.3% |
| 18. | 62.5% | 70% | 69.3% |
| 19. | 42.5% | 40.1% | 43.81% |
| 20. | 87.5% | 92% | 89.5% |
| 21. | 62.5% | 63.7% | 62.7% |
| 22. | 42.5% | 40.2% | 40.37% |

Samples were divided into: a) SVM prediction was more accurate (1, 5, 6, 8, 9, 16, 19, 20, 21), b) Q-test prediction was more accurate (3, 4, 7, 10, 11, 12, 14, 15, 17), and c) the methods were equivalent in accuracy (2, 3, 18, 22). For these 22 samples, the performance of the two methods overall was roughly equivalent, each outperforming the other in 9/22 cases.

The value of the SVM method is that it can be automated to apply to dataset which, a priori, may not have a definite criterion that can be applied, a requirement for the Q-test method. On the other hand, the Q-test method is computationally simpler, and is likely preferred for fractional abundance applications that can utilize well-characterized criterion in the Q-test format.

Example 3—Q-Test Based FA Using Short DNA (74 bp Reference, 94 bp Target Transgene) With Unique Payloads In the context of GMO % prediction applications, this example shows that two comparable lengths can be used for the target and reference dsDNA, where discrimination in nanopore event signature is achieved by using two distinct sequence-specific payloads.

Methods: Using validated qPCR primer sets (publicly available from the European Union Reference Laboratory for GM Food and Feed) we amplified both 94 bp transgene-specific and 74 bp taxon-specific fragments from mixtures of conventional and transgene-containing genomic DNA samples. Prior to nanopore detection, these amplicons were hybridized (method described in Data Storage patent #5520281-v2-29517, May 16, 2016) with sequence-specific oligonucleotide probes covalently linked to PEG polymer probes (see International Publication No. WO/2016/187159, "Methods and Compositions for Target Detection in a Nanopore Using a Labelled Polymer Scaffold," incorporated herein by reference in its entirety. Specifically, the transgene-targeting probe was linked to a 4-arm 40 kDa PEG and the reference-targeting probe was linked to an 8-arm 40 kDa PEG.

Figure 8:
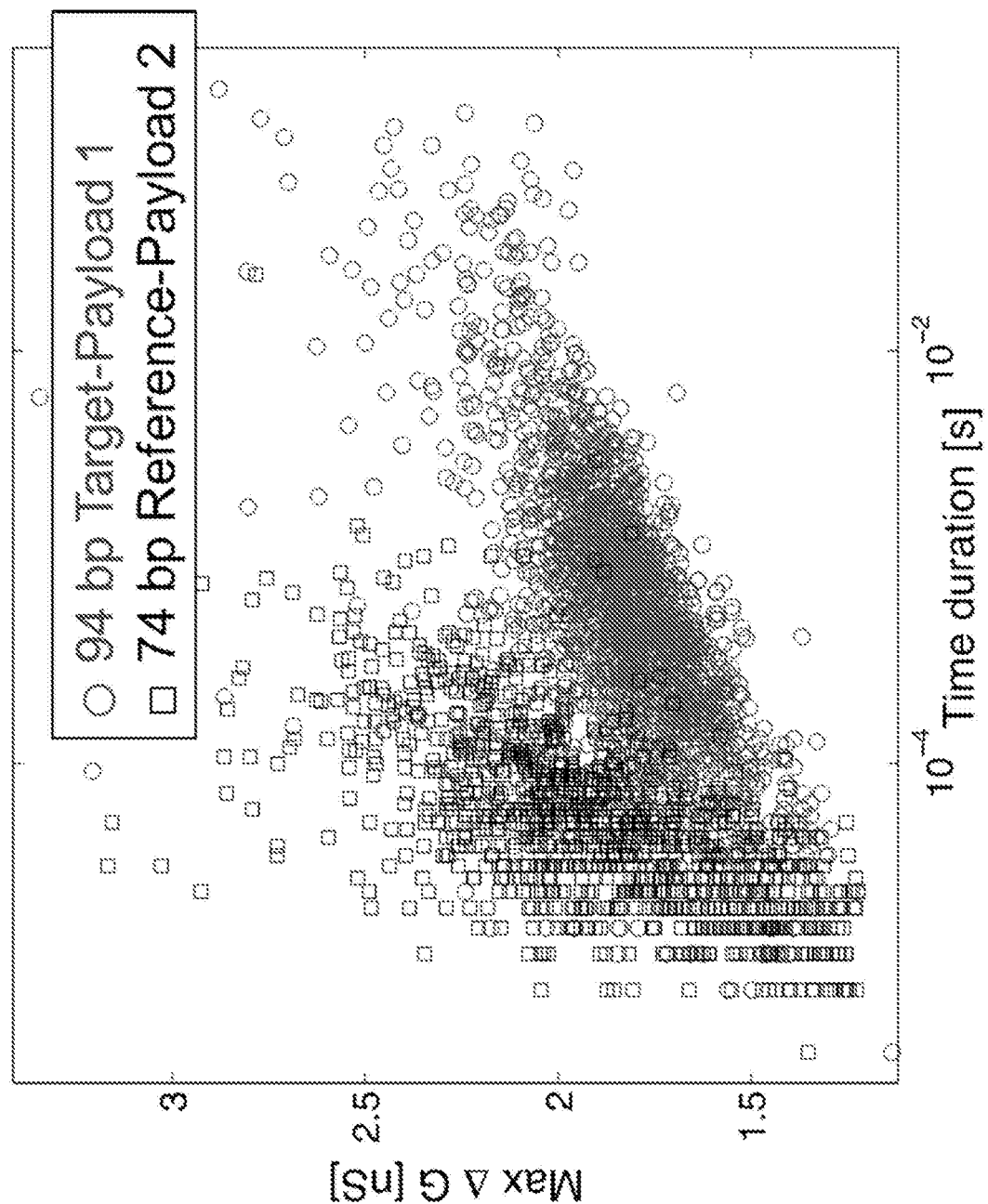
FIG. 8 shows an event plot for two molecule types (94 bp target dsDNA bound to a probe/payload and 74 bp reference dsDNA bound to a probe/payload) that were run as isolated controls sequentially on the same pore.

As a representative example of an all event scatter plot, FIG. 8 shows an event plot for two molecule types that were run as isolated controls sequentially on the same pore. First, a sample containing a 96 bp DNA/probe-payload complex was prepared and measured in a nanopore device. The complex is a model for a fragment comprising the target sequence and bound with a probe-payload. The probe-payload was a PNA-PEG with a 4-arm PEG structure. Next, the fragment comprising the reference sequence was designed to generate a unique event signature upon translocation through the nanopore with which fractional abundance calculations could be achieved. The reference molecule is a 74 bp DNA with PNA-PEG bound, where the PEG has an 8-arm structure. The key is that the reference/probe-payload molecule generates a unique event subpopulation that is distinct from the target/probe-payload molecule, and both are distinct from any background events when present.

The protocol followed on each nanopore was: a) 100% 74 bp/payload-2 reference for 5 minutes, then flush; b) 100% p4 bp/payload-1 target for 5 minutes, then flush; c) run between 1 and 4 unknowns, each for 5 minutes, flushing in-between; d) run a control mixture. Area criterion was used and a q-threshold range spanning the $75^{th}$ to the $99^{th}$ percentiles of $Q_{ref}$ was implemented, reporting the average $R^*_{mix}(q)$ as the predicted GMO %. In equation (2), the 1:1 control mixture was used for compensation for a capture rate constant differential between a target analyte and a reference analyte.

A set of nanopore experiments were performed following the protocol stated above, and each mixed sample was tested 2-4 times, always on a different nanopore, and by a different experimenter or on a different date. Nanopore size range was 25-35 nm in diameter. A total of 6 mixed samples (Sp1-Sp6) were assayed. Table 6 reports the combined estimates, ordered from smallest to largest predicted GMO % value. The reported mean GMO % values are computed by averaging the single-nanopore predictions. The uncertainty of each mean estimate is computed and reported as $95^{th}$-percentile confidence interval. The number of times each sample was tested and the true GMO % for each sample are also reported.

TABLE 6

Combined GMO % predictions using distinct payloads to discriminate target/reference

| Sample No. | No. Tests | Mean GMO % | True GMO % | Percent Error (Pred. - True) |
|---|---|---|---|---|
| Sp1 | 2 | 14.8 ± 1.8% | 10% | +4.8% |
| Sp2 | 2 | 16.8 ± 1.9% | 15% | +1.8% |
| Sp3 | 4 | 20.5 ± 1.5% | 20% | +0.5% |
| Sp4 | 2 | 22.3 ± 2.0% | 25% | −2.7% |
| Sp5 | 4 | 28.3 ± 1.7% | 30% | −1.7% |
| Sp6 | 2 | 45.8 ± 3.5% | 40% | +5.8% |

Prediction performance with the two payloads appears to be not quite as good as when using dsDNA length discrimination (Examples 1, 2). In any case, accuracy is better than 6% in all cases, and can be further improved by having more nanopores measuring the pool of molecules in parallel, and combining the resulting estimates.

Example 4—Q-Test and SVM Methods for FA of KRAS G12D SNP Compared to Wild-Type Using Short DNA (89 bp) and Two Unique Payloads We designed primers to amplify short (58 bp, 70 bp, or 89 bp) fragments of the human KRAS gene from highly fragmented, cell-free, circulating DNAs. (cfDNA primer sequences were designed to anneal on either side of KRAS G12D SNP sequence (CosmicID 521). Amplicons were generated from the cell-free circulating DNA fraction obtained from blood plasma and subject to hybridization with oligonucleotide probes targeting both wildtype and mutant KRAS alleles and covalently linked to PEG polymer payloads: probes that target the KRAS wt alleles (c.35G) were linked to either 40 kDa 8-arm or 80 kDa 2-branch PEG polymers and probes targeting the G12D (c.35G→A) allele were linked to a 40 kDa 3-branch PEG polymers.

Figure 9A:
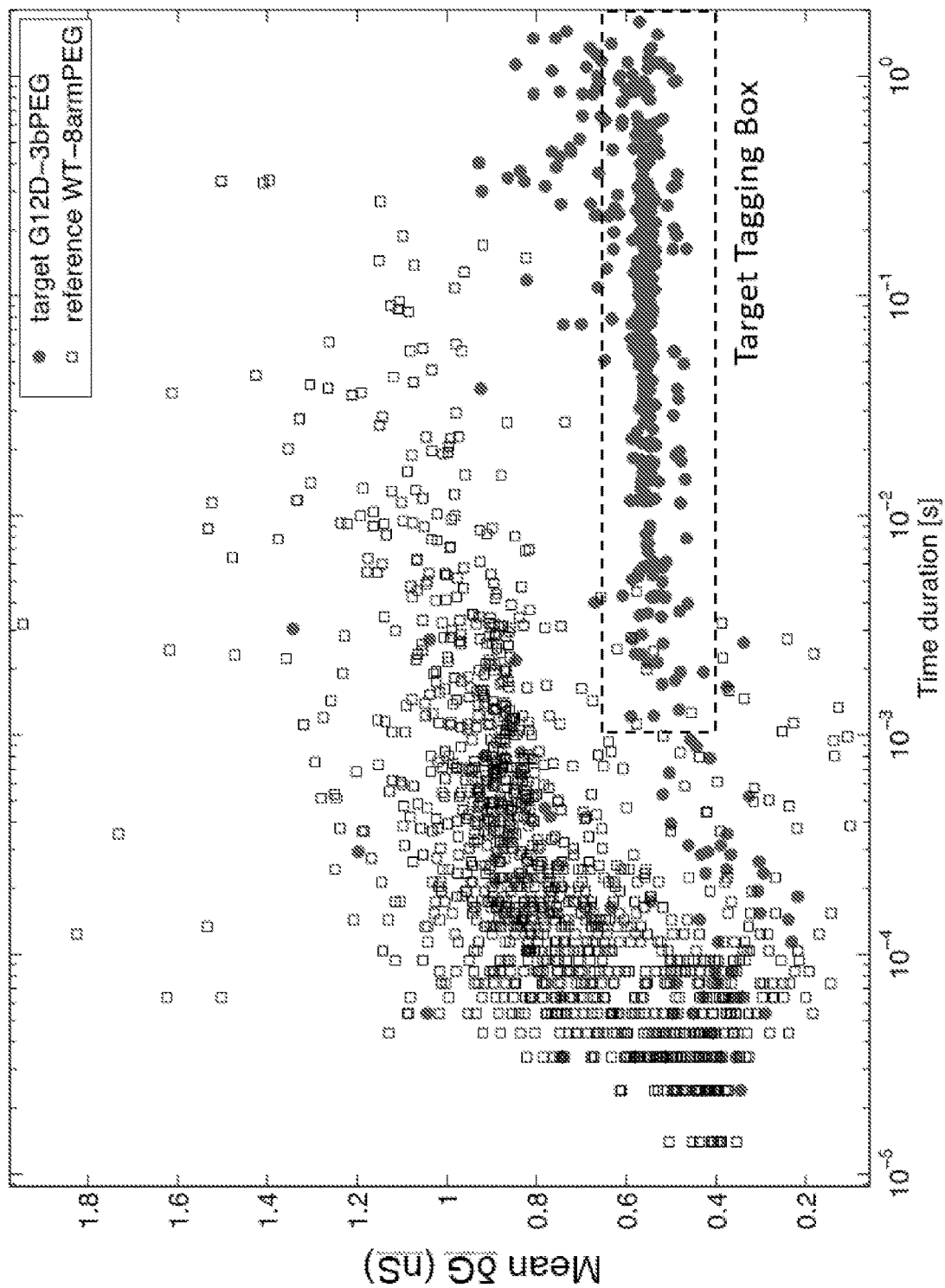
FIG. 9A shows a representative event plot of mean δG vs. duration for the 100% target analyte control sample (closed circles) and the 100% reference analyte control sample (open squares) overlaid. The target analyte is 89 bp DNA with G12D-bound probe linked to a 3-branch PEG (denoted G12D-3bPEG). The reference analyte is 89 bp DNA with wild-type (c.35G)-bound probe linked to an 8-arm PEG (denoted WT-8armPEG). The thresholds for identifying an event signature as from a target analyte passing through the nanopore ($q_1$=1 msec, $q_2$=0.4 nS and $q_3$=0.65 nS) create the target tagging box (dashed line).

FIG. 9A shows a representative event plot of mean δG vs. duration for the 100% target analyte control sample (blue closed circles) and the 100% reference molecule control sample (black open squares) overlaid. The target analyte was 89 bp DNA with G12D-bound probe linked to a 3-branch PEG (denoted G12D-3bPEG). The reference molecule was 89 bp DNA with wild-type (c.35G)-bound probe linked to an 8-arm PEG (denoted WT-8armPEG). The two controls were run sequentially using a 35 nm diameter nanopore at 215 mV (1.0 M LiCl 10 mM tris 1 mM EDTA). Visually, the plot suggests a criterion based on three inequalities for tagging target events:

duration≥$q_1$
mean δG≥$q_2$
mean δG≥$q_3$

Figure 9B:
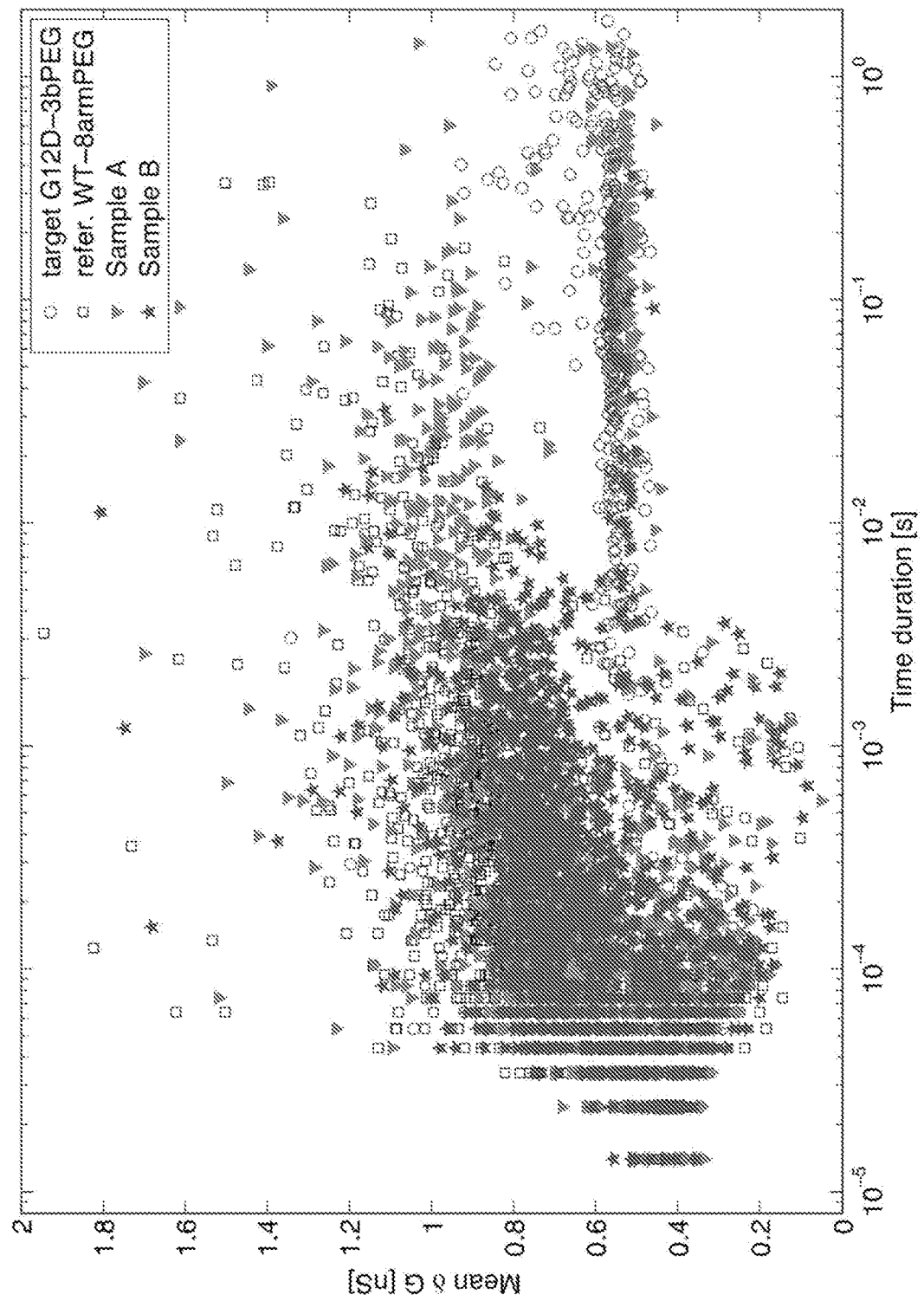
FIG. 9B shows the plot from FIG. 9A, with data from unknown sample A (triangle) and sample B (star) comprising target analytes and reference analytes overlaid onto the plot.

The thresholds $q_1$=1 msec, $q_2$=0.4 nS and $q_3$=0.65 nS create the target tagging box (dashed line) also shown in FIG. 9A. Using the criterion of the three inequalities with stated thresholds, the isolated controls produce $Q_{ref}$=0.006 and $Q_{targ}$=0.795. An equimolar concentration of target-payload and reference-payload molecules resulted in $Q_{1:1}$=0.274, used as the control mixture. Two subsequent unknown samples, A and B, registered $Q_A$=0.066 and $Q_B$=0.041. The two samples are overlaid on the two isolated controls in an event plot, shown in FIG. 9B. Visually, sample A shows higher G12D content than sample B, though both are positive compared to the 0.6% false positive rate of the 100% WT control. After applying equation (1) and using the control mixture for compensation, the predicted fractions of G12D mutant to wild type are $F^*_A$=11.1±0.9% and $F^*_B$=6.0±0.7% for samples A and B, respectively.

Table 7 shows the results for samples A and B in rows 1 and 2. Also shown are the results for all patient samples tested. A total of 5 different patient samples were assayed. Samples C and C2 were subsamples from the same patient sample; likewise for sample D, D2 and E, E2. Different subsamples taken from the same patient sample were, in all three cases considered, within 2% of one another. This is despite different people running each nanopore experiment on a different nanopore, and in two cases on a different day. This suggests a reproducible workflow and quantitative fractional abundance method.

TABLE 7

Predicted G12D mutant fraction in blood samples using Q-test method

| Nanopore ID, diameter | Sample Label | Estimated G12D Fraction % | Total Events |
|---|---|---|---|
| NP1, 35 nm | A | 11 ± 0.89% | 1,494 |
| NP1, 35 nm | B | 6.9 ± 0.75 | 1,508 |
| NP2, 30 nm | C | 7 ± 0.9% | 1,488 |
| NP3, 33 nm | D | 5.9 ± 0.5% | 2,503 |
| NP4, 33 nm | C2 | 5.3 ± 0.9% | 1,188 |
| NP5, 38 nm | D2 | 6.5 ± 1.0% | 1,741 |

TABLE 7-continued

Predicted G12D mutant fraction in blood samples using Q-test method

| Nanopore ID, diameter | Sample Label | Estimated G12D Fraction % | Total Events |
|---|---|---|---|
| NP6, 23 nm | E | 30 ± 0.9% | 2,455 |
| NP7, 32 nm | E2 | 28 ± 0.9% | 3,299 |

The true amount of G12D is unknown for these samples. Samples were collected from patients several weeks after the onset of cancer treatment (chemotherapy), and after each patients DNA was sequence and found to be positive for the G12D mutation. Non positive control samples from a control patient were also assayed, and the predicted fraction of G12D was 2% or less, suggesting a total workflow false positive of 2%. Further optimization in the workflow can reduce the limit of detection further.

Figure 10:
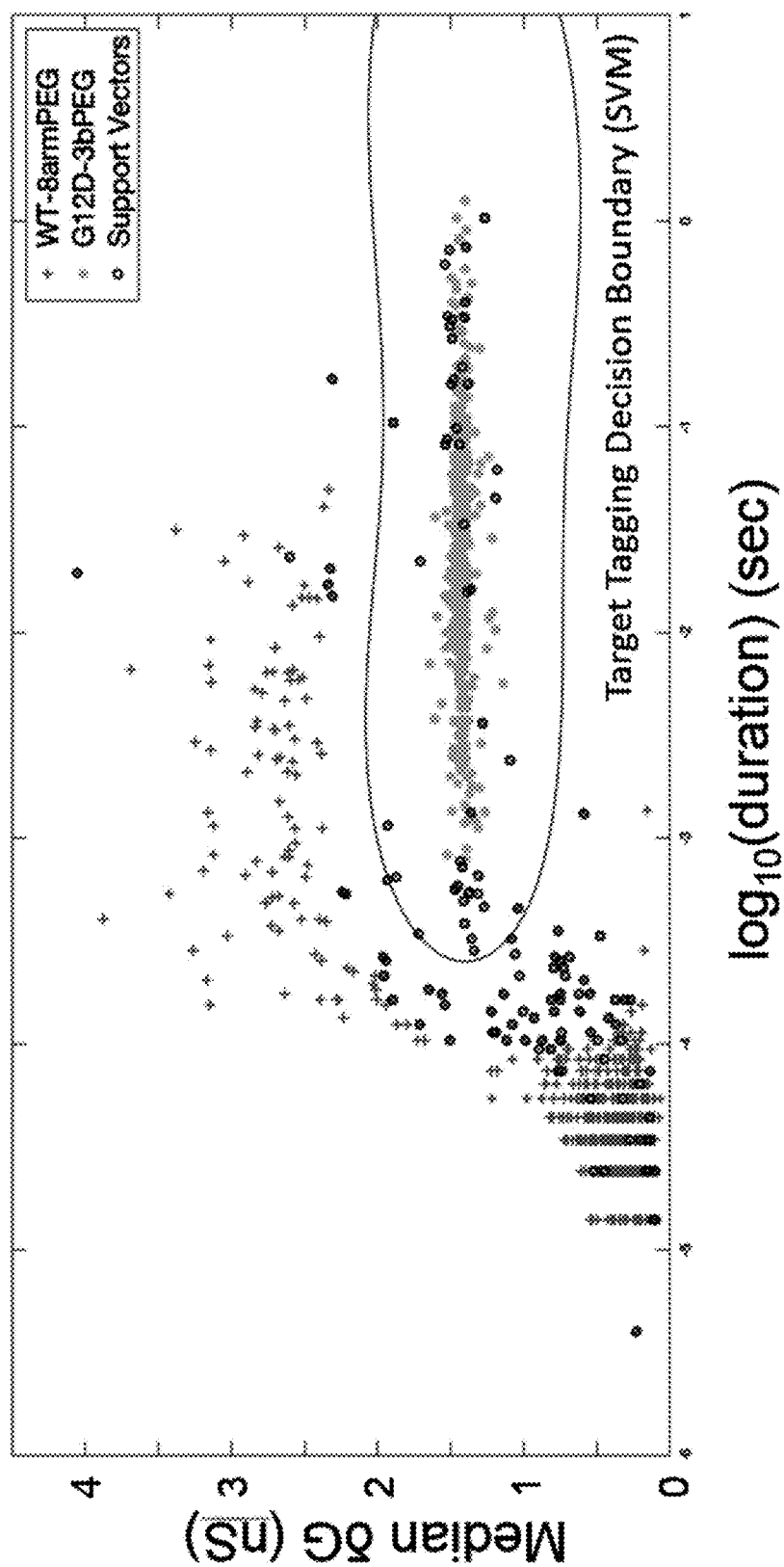
FIG. 10 shows a representative event plot of mean δG vs. duration for the 100% target analyte control sample (closed circles) and the 100% reference analyte control sample (open squares) overlaid. Also plotted is the support vector machine-identified decision boundary (i.e. threshold) for discriminating target analytes from reference analytes.

The SVM method was applied for comparison. Using one representative experiment (nanopore NP4 in Table 1), the data was processed using the steps described for applying the SVM method. An event scatter plot of median δG vs. $\log_{10}$(duration) is shown in FIG. 10 for the 100% reference control and the 100% target control overlaid. Also plotted is the SVM-identified decision boundary. The predicted G12D fraction in sample C2 is reported in Table 8 for both the Q-test and SVM methods. The two methods are within 5% of each other.

TABLE 8

Predicted G12D fraction using the Q-test and SVM to determine an optimized threshold (q).

| Nanopore ID | Sample Label | Q-test G12D Frac. (%) | SVM G12D Frac. (%) |
|---|---|---|---|
| NP4 | C2 | 5.3% | 10.4% |

Example 5: EMGM for FA of KRAS G12D SNP Compared to Wild-Type Using Short DNA (89 bp) and Two Unique Payloads Application of Expectation Maximization Algorithm for Gaussian Mixtures (EMGM) to a representative data set is described. The target and reference are the mutant KRASG12D SNP and wild-type sequences within payload-bound dsDNA fragments, as described in Example 4. In a representative workflow, only a 1:1 control mixture was measured and only one 100% reference control was measured, followed by the unknown mixture.

Figure 11:
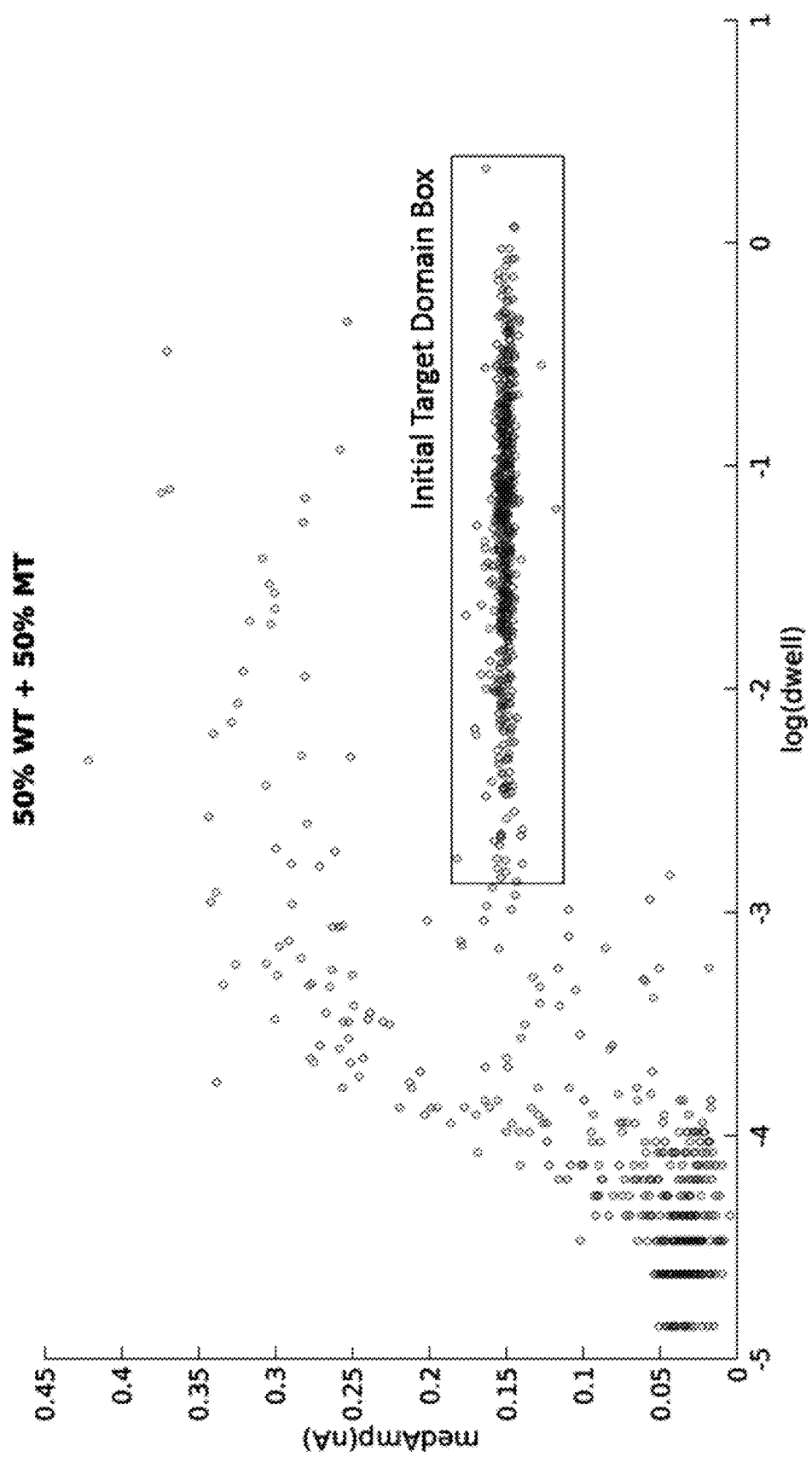
FIG. 11 shows events from a 50% target/50% reference mixture sample plotted on an all-event scatter plot of max δG versus duration. The target domain box encompasses events associated with a probe-bound mutant targets.

Step 1: log of dwell time (log(dwell)) and median amplitude (medAmp) of 50% target & 50% reference mixture sample was used as input data for the EMGM algorithm (FIG. 11). The initially identified expected region of the target, the mutant KRASG12D SNP, is marked as the rectangular region in the plot, using previously established knowledge about this assay. The prior knowledge was established by testing the 100% target control in comparable conditions (same buffer) in separate experiments. The box is not used for tagging. Rather, after the EMGM is applied to the control mixture, any events associated with a Gaussian mixture within the box are tagged as target events.

Figure 12:
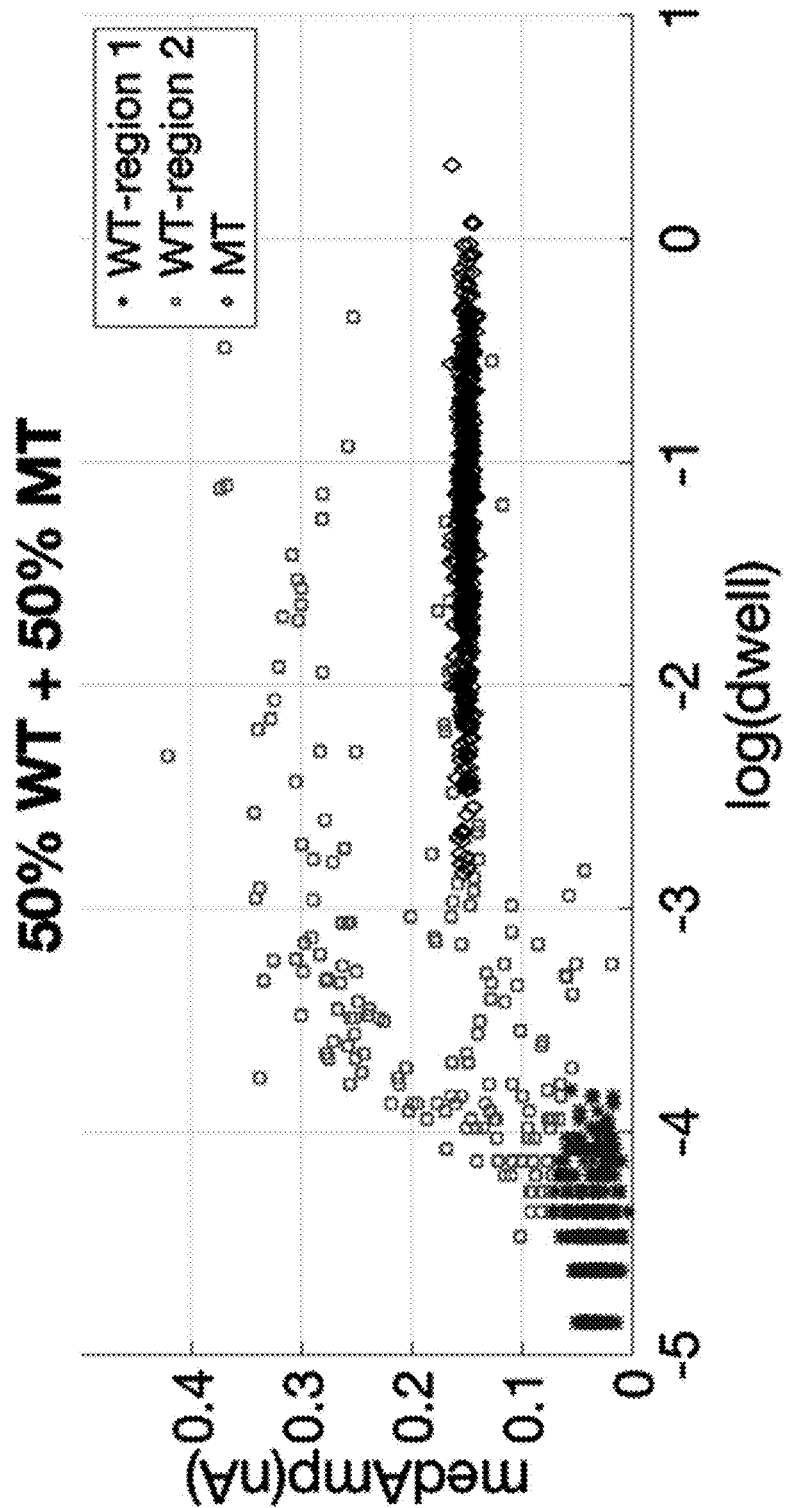
FIG. 12 shows the results of application of Expectation Maximization Algorithm for Gaussian Mixtures (EMGM) using a 3-Gaussian mixture model to the data from a 50% target/50% reference mixture sample shown in FIG. 11 for identification of target (mutant) and reference (wild-type) populations.

Step 2: Based on the population, a 3-Gaussian mixture model was used to train the model. This model predicted the mutant (target) region in one cluster (diamond). The other 2 clusters (star and square) correspond to wild-type (FIG. 12). We observe that some events within the initial target domain box (FIG. 11) are associated with the reference modes by the EMGM algorithm. This is different than the Q-test method, where the box itself defines the population of events that are tagged as targets vs. reference.

Figure 13:
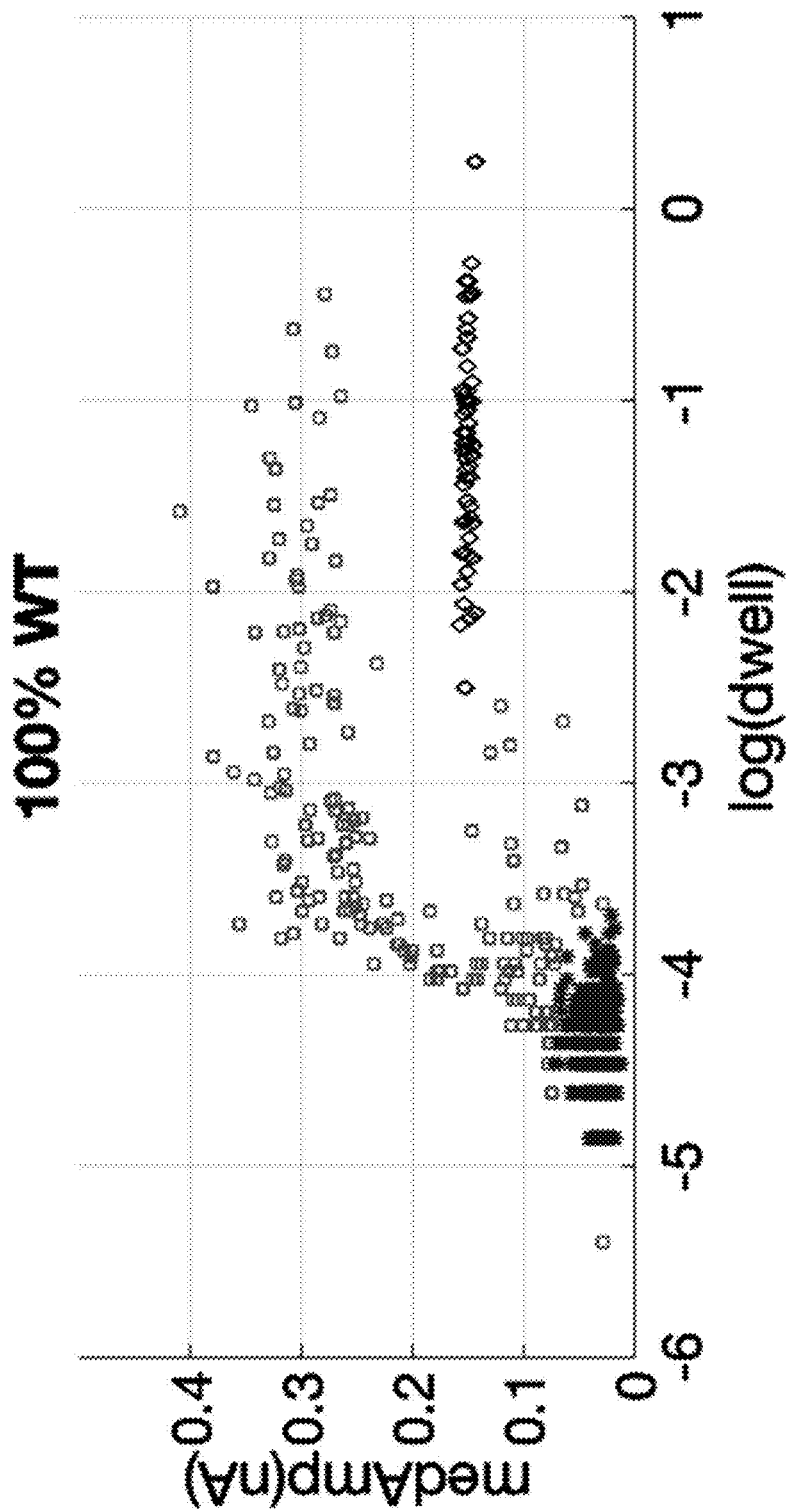
FIG. 13 shows the results of application of EMGM using a 3-Gaussian mixture model to data from a reference-only control sample to establish a false positive fraction.

Step 3: The model was applied on 100% wild-type (reference) sample. The ratio number of events in the mutant (target) region over the total number of events establishes the false positive fraction (FIG. 13), which can be used to improve the fractional abundance estimate.

Figure 14:
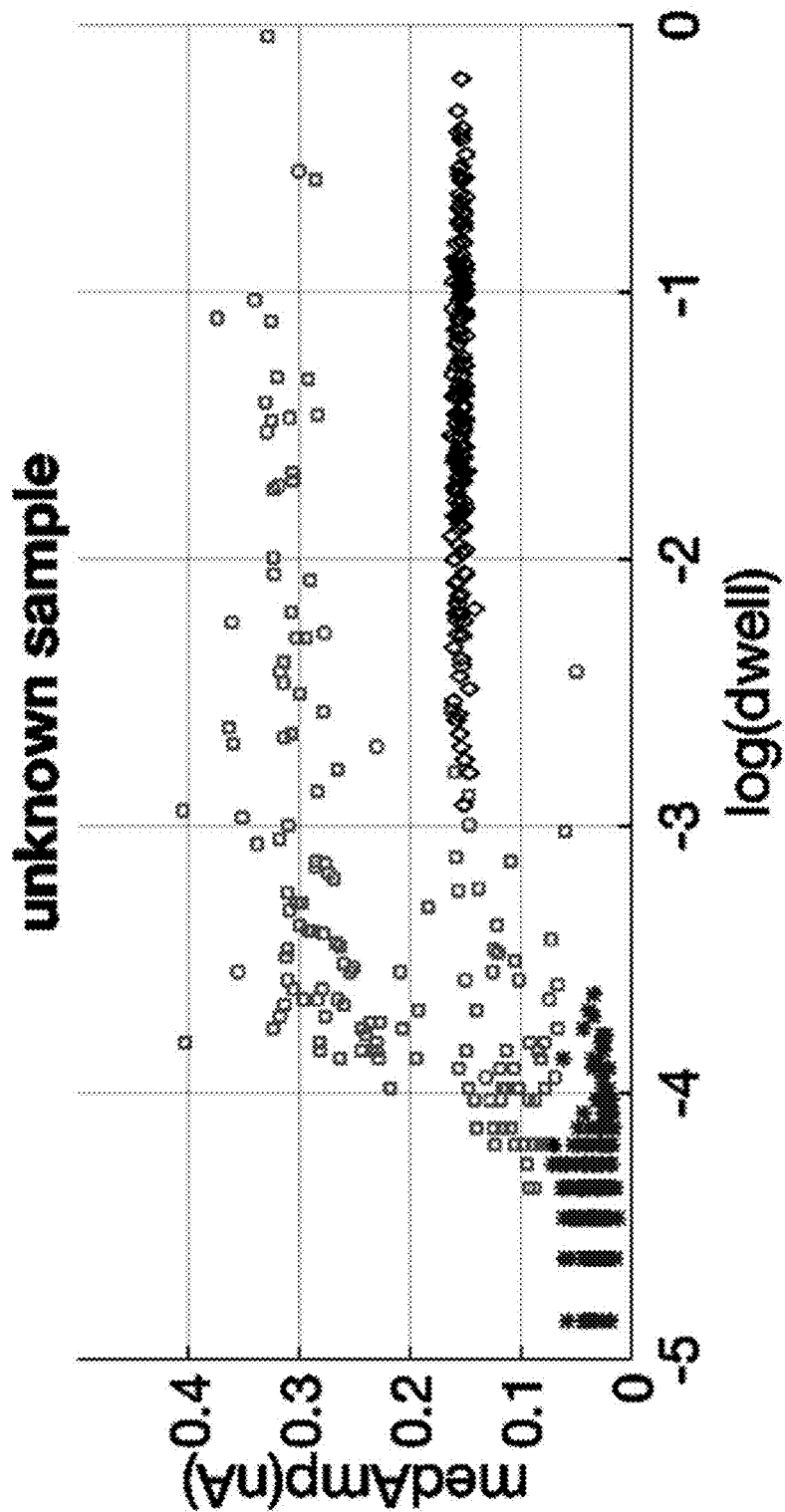
FIG. 14 shows the results of application of EMGM using a 3-Gaussian mixture model to data from a mixed unknown sample to identify a relative abundance of mutant (target) molecules in the unknown sample.

Step 4: The model was used to predict unknown mixtures. The ratio number of events in mutant region over the total number of events was used a predictor of the percentage of mutant molecules in unknown mixture (FIG. 14).

As a test of performance enhancement by false positive compensation, the false positive fraction from step 3 was subtracted from computed fraction in step 4 as a correction. The results of applying EMGM to multiple mixtures within a set of nanopore experiments are reported in Table 9. Mixtures were blinded until EMGM results were assembled, and then the results were compared to the true G12D fractional abundance values.

TABLE 9

Predicted G12D fraction comparing the EMGM without and with false positive (FP) compensation

| Nanopore ID | Known G12D Frac. (%) | EMGM G12D Frac. (%) | EMGM + FP-comp G12D Frac. (%) |
|---|---|---|---|
| NP-a | 50% | 50.7% | 43.2% |
|  | 20% | 28.1% | 20.5% |
|  | 10% | 13.3% | 5.7% |
| NP-b | 50% | 56.4% | 47.3% |
|  | 20% | 31.5% | 22.4% |
|  | 10% | 19.9% | 10.8% |
| NP-c | 50% | 50.8% | — |
|  | 20% | 19.7% | — |
|  | 10% | 5.3% | — |

In the case of NP-a, performance was enhanced only in the 20% case by using false positive compensation. For NP-b, performance was enhanced in all cases. False positive compensation was not tested for NP-c, although performance was already good, particularly for the 50% and 20% estimates.

In summary, only a control mixture is needed to apply the EMGM method, prior to applying the EMGM models to an unknown mixture for fractional abundance estimation.

Other Embodiments

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

What is claimed is:

1. A method of a determining an improved estimate of a true relative abundance of a target analyte in a mixed unknown sample using a nanopore device, comprising applying a voltage across a nanopore in a nanopore device to generate a detectable electronic signature and to induce translocation of charged analytes, including target analytes and reference analytes, through said nanopore separately for each of:
   a control sample comprising a known relative abundance of said target analytes to said reference analytes, and
   said mixed unknown sample comprising said target analytes and said reference analytes, wherein the relative abundance of said target analytes in said mixed unknown sample is to be determined;

generating a plurality of event signatures generated by translocation of said target analytes and said reference analytes through said nanopore for each of said control sample and said mixed unknown sample;

identifying a quantity of first event signatures associated with said target analyte and a quantity of second event signatures associated with said reference analyte from said plurality of event signatures to determine a detected relative abundance of first and second event signatures for each of said control sample and said mixed unknown sample; and adjusting a detected relative abundance of said first and second event signatures in said mixed unknown sample using the detected relative abundance of said first and second event signatures in said control sample to correct for an error in the detected relative abundance, thereby determining an improved estimate of the true relative abundance of said target analyte in said mixed unknown sample.

2. The method of claim 1, wherein said control sample is a target control sample comprising said target analytes, but not said reference analytes.

3. The method of claim 1, wherein said control sample is a reference control sample comprising said reference analytes, but not said target analytes.

4. The method of claim 3, further comprising applying a voltage to a nanopore device to induce translocation of charged analytes through a nanopore sensor for a target control sample comprising said target analytes, but not said reference analytes.

5. The method of claim 4, wherein said adjustment of said detected relative abundance of said first and second event signatures in said mixed unknown sample comprises using the detected relative abundance of said first and second event signatures in said target control sample and in said reference control sample to correct for said error in the detected relative abundance.

6. The method of claim 1, wherein said error comprises a false positive or a false negative detection error of said target analyte.

7. The method of claim 1, further comprising applying a voltage to a nanopore device to induce translocation of charged analytes through a nanopore sensor for a mixed control sample comprising said target analytes and said reference analytes, wherein the relative abundance of said target analytes and said reference analytes is known.

8. The method of claim 7, wherein said adjustment of said detected relative abundance of said first and second event signatures in said mixed unknown sample comprises using the detected relative abundance of said first and second event signatures in said mixed control sample to correct for said error in the detected relative abundance.

9. The method of claim 1, wherein said error comprises a false positive target analyte detection error, a false negative target analyte detection error, a capture rate constant differential between said target analyte and said reference analyte, or any combination thereof.

10. The method of claim 1, wherein said control sample is a mixed control sample comprising said target analytes and said reference analytes, wherein the relative abundance of said target analytes and said reference analytes is known.

11. The method of claim 10, wherein said error comprises a capture rate constant differential between said target analyte and said reference analyte.

12. The method of claim 7, wherein said mixed control sample comprises a relative abundance of said target analytes to said reference analytes that differs by no more than a factor of 1.2, a factor of 1.5, a factor of 2, a factor of 5, or a factor of 10 relative to said mixed unknown sample.

13. The method of claim 1, wherein said estimate of the true relative abundance is an estimate of a true ratio of said target analyte to said reference analyte in said mixed unknown sample.

14. The method of claim 13, wherein said estimate ($R^*_{mix}$) of the true ratio is determined by $R^*_{mix} = \rho\alpha$, wherein the parameter $\rho$ is an estimate for a ratio that can compensate for a false positive detection error, a false negative detection error, or both, and wherein the parameter $\alpha$ can be used to compensate for a capture rate constant differential between said target analyte and said reference analyte.

15. The method of claim 14, wherein $\alpha$ is an estimate of a ratio of the reference analyte capture rate divided by the target analyte capture rate.

16. The method of claim 1, wherein said estimate of the true relative abundance is an estimate of a true fraction of said target analytes in a population of said reference analytes and said target analytes in said mixed unknown sample.

17. The method of claim 16, wherein said estimate of the true fraction ($F^*_{mix}$) is determined by $$F^*_{mix} = \frac{\rho\alpha}{\rho\alpha + 1},$$

wherein the parameter $\rho$ is an estimate for a ratio that can compensate for a false positive detection error, a false negative detection error, or both, and wherein the parameter $\alpha$ can be used to compensate for a capture rate constant differential between said target analyte and said reference analyte.

18. The method of claim 17, wherein $\alpha$ is an estimate of a ratio of the reference analyte capture rate divided by the target analyte capture rate.

19. The method of claim 14, wherein $$\rho = \left(\frac{Q_{mix} - Q_{ref}}{Q_{targ} - Q_{mix}}\right), \text{ and } \alpha = \left(\frac{Q_{targ} - Q_{X:Y}}{Q_{X:Y} - Q_{ref}}\right) \times \frac{X}{Y}.$$

20. The method of claim 19, wherein $Q_{targ}$ is the fraction of said first event signature observed in said control sample if said control sample is a target control sample comprising said target analytes but not said reference analytes, or $Q_{targ}=1$ if said control sample is not a target control sample.

21. The method of claim 19, wherein $Q_{ref}$ is the fraction of said second event signature observed in said control sample if said control sample is a reference control sample comprising said reference analytes but not said target analytes, or $Q_{ref}=0$ if said control sample is not a reference control sample.

22. The method of claim 19, wherein $Q_{X:Y}$ is the fraction of said first event signature observed in said mixed control sample and wherein $$\frac{X}{Y}$$

is the known ratio of target analytes (X) to reference analytes (Y) in the mixed control sample if said control sample is used, or $\alpha=1$ if no mixed control sample is used.

23. The method of claim 19, wherein $Q_{mix}$ is the fraction of said first event signature observed in said mixed unknown sample.

24. The method of claim 1, wherein said mixed unknown sample or said control sample is prepared by nucleic acid amplification.

25. The method of claim 1, wherein said mixed unknown sample or said control sample is not prepared by nucleic acid amplification.

26. The method of claim 1, wherein said mixed unknown sample is purified to substantially consist of said reference analytes and said target analytes.

27. The method of claim 1, wherein said unknown mixed sample is not purified.

28. The method of claim 1, wherein the quantity or concentration of said reference analytes in said mixed unknown sample are known.

29. The method of claim 28, further comprising determining an estimate of the absolute quantity or concentration of said target analytes in said mixed unknown sample using said estimate of the true relative abundance of said target analytes to said reference analytes in said mixed unknown sample and said known quantity or concentration of said reference analytes in said mixed unknown sample.

30. The method of claim 1, wherein said quantity of first event signatures associated with said target analyte and said quantity of second event signatures associated with said reference analyte are identified according to a defined threshold.

31. The method of claim 30, further comprising optimizing said threshold to increase accuracy of detection of said reference analytes and/or said target analytes using a Q-test, a support vector machine, or an expectation maximization algorithm.

32. The method of claim 31, wherein said support vector machine is trained using electronic signatures from control samples comprising known quantities of target analytes and reference analytes.

33. The method of claim 30, wherein said defined threshold is a function of one or more features of an event signature selected from the group consisting of: an event duration, a maximum $\delta G$, a median $\delta G$, an average $\delta G$, a standard deviation of the event signature, a mean or median of the noise power of the event below 50 Hz, a unique pattern in said event signature, an area of an event, or any combination thereof.

34. The method of claim 1, wherein said adjustment of said detected relative abundance of said first and second event signatures in said mixed unknown sample to correct for said error in the detected relative abundance is performed using a Q-test, a support vector machine, or an expectation maximization algorithm.

35. The method of claim 1, wherein said target analyte and said reference analyte each comprise a polynucleotide.

36. The method of claim 35, wherein said target analyte polynucleotide and said reference analyte polynucleotide are of different lengths.

37. The method of claim 36, wherein said lengths are different by at least 10 nucleotides, at least 20 nucleotides, at least 50 nucleotides, at least 100 nucleotides, at least 150 nucleotides or at least 200 nucleotides.

38. The method of claim 1, further comprising contacting said control sample or said mixed unknown sample with a first probe bound to a first payload, wherein said first probe is configured to bind specifically to said target analytes.

39. The method of claim 1, further comprising contacting said control sample or said mixed unknown sample with a second probe bound to a second payload, wherein said second probe is configured to bind specifically to said reference analytes.

40. The method of claim 1, wherein said target analyte is correlated with a genetically modified organism.

41. The method of claim 1, wherein said target analyte comprises a marker associated with the presence or absence of cancer in a patient.

* * * * *